United States Patent [19]

Wilson et al.

[11] Patent Number: 5,465,841
[45] Date of Patent: Nov. 14, 1995

[54] MEDICAL WASTE COLLECTION AND TREATMENT STATION

[75] Inventors: Joseph H. Wilson, Speedway; David B. Mennel; Jeffrey C. Rapp, both of Greenwood, all of Ind.

[73] Assignee: Ecomed, Inc., Indianapolis, Ind.

[21] Appl. No.: 73,758

[22] Filed: Jun. 8, 1993

Related U.S. Application Data

[63] Continuation-in-part of Ser. No. 882,915, May 19, 1992, Pat. No. 5,236,135, which is a continuation-in-part of Ser. No. 704,455, May 23, 1991, Pat. No. 5,240,187.

[51] Int. Cl.⁶ .......................... B65D 83/10; B65D 43/16
[52] U.S. Cl. .......................... 206/366; 220/23.83; 220/263; 220/909; 312/209
[58] Field of Search .................................. 220/909, 908, 220/263, 23.83; 312/138.1, 209, 245; 206/366, 365, 364

[56] References Cited

U.S. PATENT DOCUMENTS

| | | |
|---|---|---|
| 1,592,601 | 7/1926 | Hines . |
| 2,557,420 | 6/1951 | Elliott ..................... 206/366 |
| 2,635,784 | 4/1953 | Bering et al. . |
| 2,660,210 | 11/1953 | Berglind . |
| 2,820,595 | 1/1958 | Schumacher . |
| 2,985,285 | 5/1961 | Riddle ..................... 206/366 |
| 3,156,278 | 11/1964 | Otto . |
| 3,389,864 | 6/1968 | Topinka . |
| 3,434,518 | 3/1969 | Motis . |
| 3,528,469 | 9/1970 | Mantelet . |
| 3,596,692 | 8/1971 | Swanke . |
| 3,814,332 | 6/1974 | Nakao . |
| 3,901,349 | 8/1975 | DeNoyer . |
| 4,194,697 | 3/1980 | Lembeck . |
| 4,269,364 | 5/1981 | Moriconi et al. . |
| 4,275,848 | 6/1981 | Webb, Sr. . |
| 4,578,185 | 3/1986 | Wilson et al. . |
| 4,586,666 | 5/1986 | Fox . |
| 4,609,156 | 9/1986 | Boele . |
| 4,618,103 | 10/1986 | Wilson et al. . |
| 4,619,409 | 10/1986 | Harper et al. . |
| 4,637,561 | 1/1987 | Edberg . |
| 4,801,034 | 1/1989 | Sandomeno ..................... 220/23.83 |
| 4,809,850 | 3/1989 | Laible et al. ..................... 206/366 |
| 4,809,915 | 3/1989 | Koffsky et al. . |
| 4,816,307 | 3/1989 | Honeycutt . |
| 4,852,814 | 8/1989 | Amiot et al. . |
| 4,860,961 | 8/1989 | Hilgarth . |
| 4,878,627 | 11/1989 | Otto . |
| 4,884,756 | 12/1989 | Pearson . |

(List continued on next page.)

FOREIGN PATENT DOCUMENTS

| | | |
|---|---|---|
| 1394972 | 2/1964 | France . |
| 0194339 | 9/1986 | Germany ..................... 220/909 |
| 61-25432 | 2/1986 | Japan . |
| 725700 | 4/1980 | U.S.S.R. . |
| 1142167 | 2/1985 | U.S.S.R. . |
| 1546076A1 | 2/1990 | U.S.S.R. . |
| 9117099 | 4/1990 | WIPO ..................... 206/366 |
| 9008713 | 8/1990 | WIPO ..................... 206/366 |

Primary Examiner—Bryon P. Gehman
Attorney, Agent, or Firm—Willian Brinks Hofer Gilson & Lione

[57] ABSTRACT

A method and apparatus for the collection and treatment of contaminated medical waste, including solid and non-solid, potentially infectious materials, permits the collection of such medical waste at the point and at the time of its generation in a solid container. The contained medical waste can be subsequently transported for pulverization, disinfection and safe disposal. A separate portable processing chamber to treat medical waste, can be used at locations remote from its power unit for the collection of medical waste and then moved to the location of the power unit to drive the waste-treatment apparatus within the chamber. In addition, a medical waste collection station can provide single and multiple containers, which may be sequentially used, for the collection of medical waste and whose use may be combined with a processing chamber to treat collected medical waste before its disposal.

22 Claims, 18 Drawing Sheets

U.S. PATENT DOCUMENTS

| | | |
|---|---|---|
| 4,889,290 | 12/1989 | Koffsky et al. . |
| 4,919,264 | 4/1990 | Shinall ................................. 206/366 X |
| 4,955,548 | 9/1990 | Rahill . |
| 4,971,261 | 11/1990 | Solomons . |
| 4,972,950 | 11/1990 | Shillington ............................. 206/366 |
| 4,984,747 | 1/1991 | Lechner . |
| 4,984,748 | 1/1991 | Kimura . |
| 5,018,675 | 5/1991 | Gateaud . |
| 5,022,548 | 6/1991 | Stakis ..................................... 220/23.83 |
| 5,054,696 | 10/1991 | Mennel et al. . |
| 5,086,922 | 2/1992 | Sagstetter et al. ...................... 206/366 |
| 5,111,958 | 5/1992 | Witthoeft ......................... 220/23.83 X |
| 5,117,997 | 6/1992 | Fink ..................................... 220/909 X |
| 5,167,343 | 12/1992 | Winfrey et al. ..................... 220/909 X |
| 5,174,468 | 12/1992 | Holderman et al. ............... 220/909 X |
| 5,236,135 | 8/1993 | Wilson et al. . |
| 5,240,108 | 8/1993 | Tonna ..................................... 206/366 |
| 5,240,187 | 8/1993 | Wilson . |
| 5,273,161 | 12/1993 | Sagstetter ................................ 206/366 |

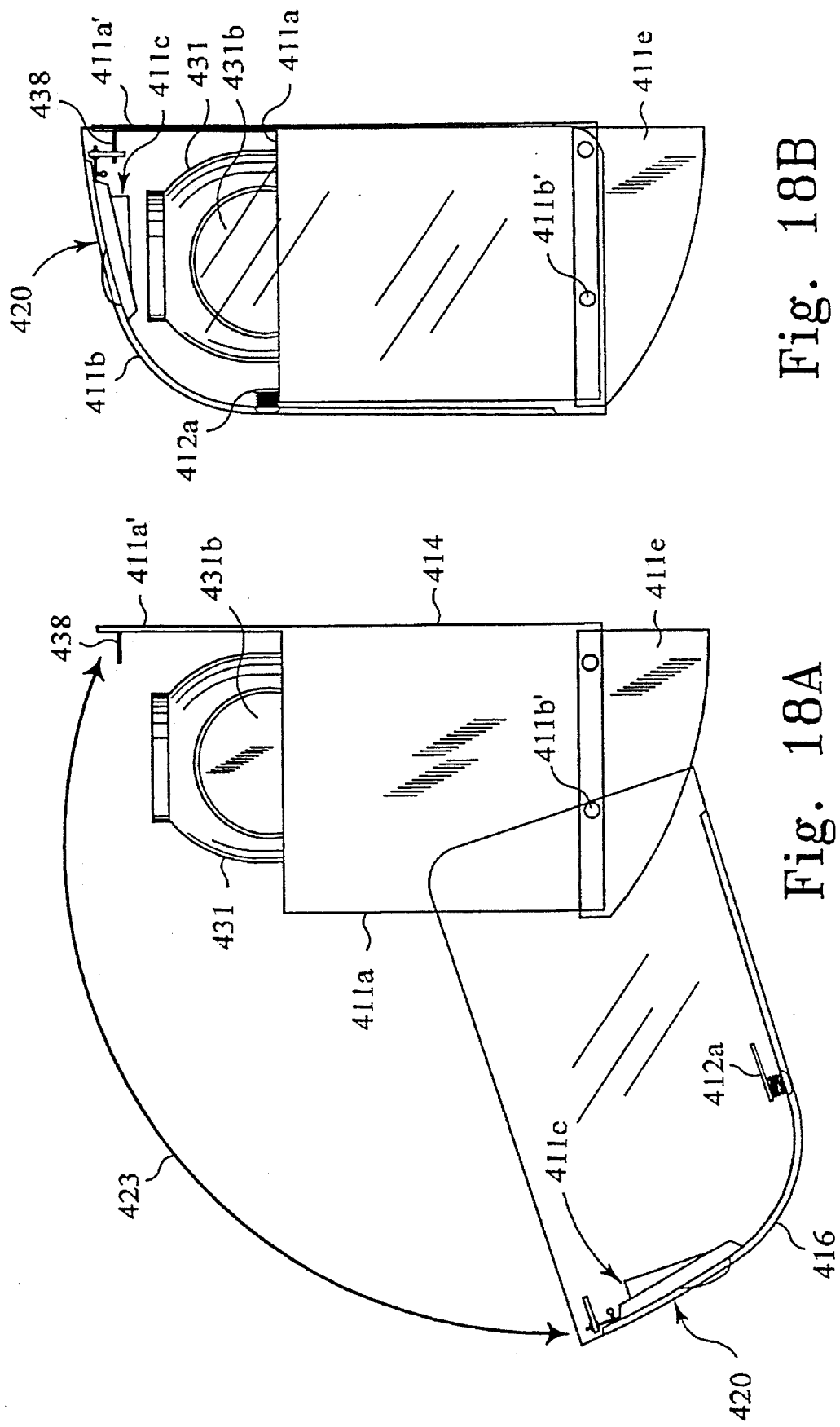

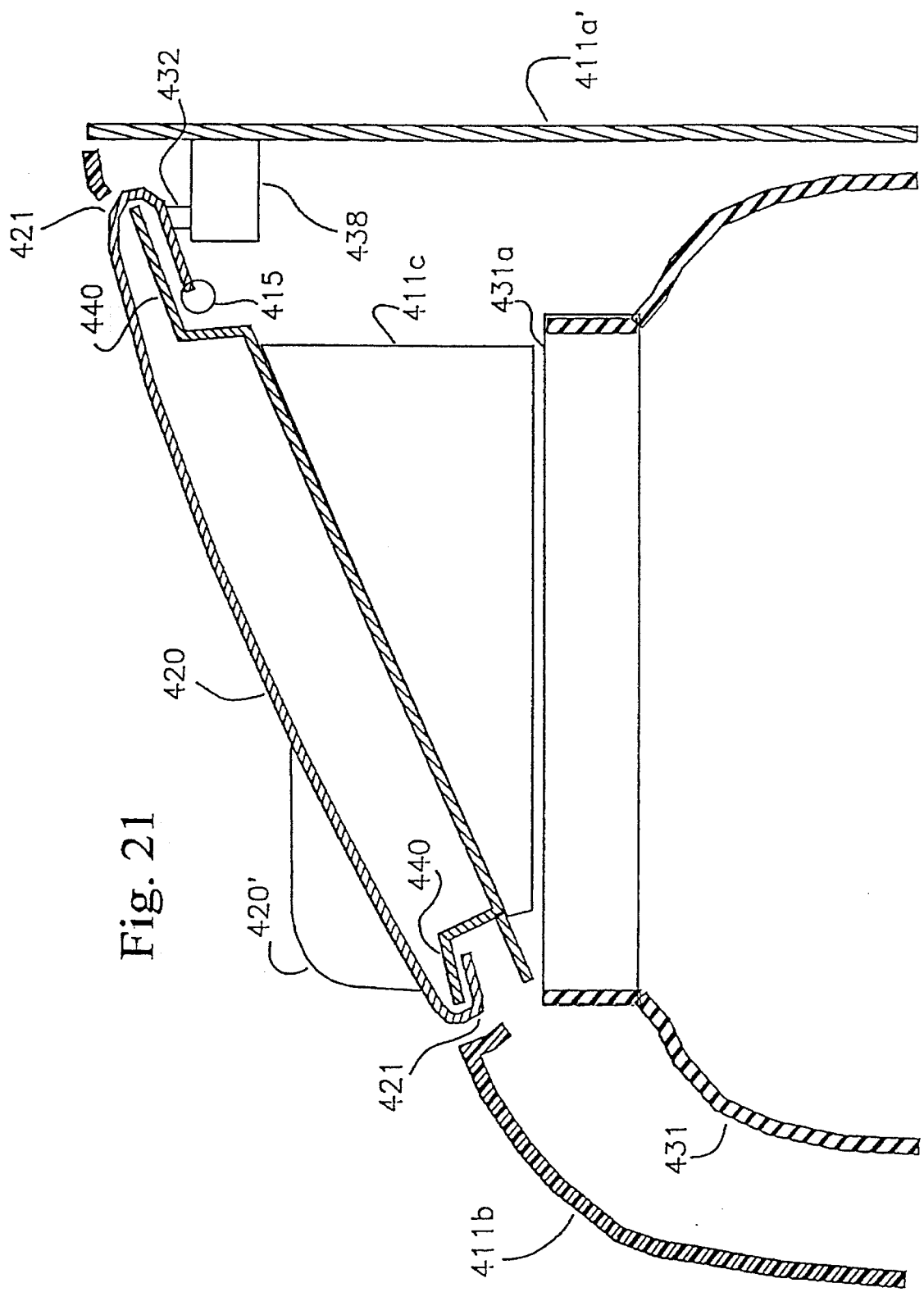

MEDICAL WASTE COLLECTION AND TREATMENT STATION

This is a continuation-in-part of U.S. patent application Ser. No. 07/882,915 filed May 19, 1992, now U.S. Pat. No. 5,236,135, which in turn is a continuation-in-part of U.S. Ser. No. 07/704,455 filed May 23, 1991, now U.S. Pat. No. 5,240,187, the disclosures of which are incorporated herein by reference.

FIELD OF THE INVENTION

This invention relates generally to methods and apparatus for handling and treating medical waste materials, and more particularly to methods and apparatus for decontaminating and rendering infectious solid and soft medical waste items handleable, and to a new medical waste collection station providing a plurality of medical waste containers which may be filled sequentially.

DESCRIPTION OF THE PRIOR ART

The treatment of medical waste with one machine is disclosed in U.S. Pat. No. 4,619,409 issued Oct. 28, 1986. It is a comparatively large stationary machine for disintegration and decontamination of hospital waste materials in relatively large volumes. Other patents also disclose medical waste treatment apparatus for hospital use, including U.S. Pat. Nos. 4,578,185; 4,618,103; and 5,054,696. But there are many facilities which do not have such volumes of waste materials, space for such a large machine, or funds to buy such large and expensive machines. A couple of examples are medical and dental offices. One effort to deal with the waste materials of such facilities is represented in U.S. Pat. No. 4,971,261 issued Nov. 20, 1990 to Solomons. That patent discloses a device that is intended to be a portable desk-top device. It has a cylindrical body 11, cover 12, one-way feed opening 13 in the cover 12, a motor driven rotating blade 20 in the body to fragment the waste, a sweeper blade agitation member 21 rotated by the blade drive motor, and a cut-out 12C of the cover 12 which can be rotated to a position of registry with a discharge opening 14 in the cylindrical body 11 and which communicates with the disposal chute 15 for discharge of the fragmented particles into the jar 23 which contains sterilizing solution. Then the jar, with sanitized and fragmented items is said to be disposed of as ordinary trash. Solomons apparently was not intended to deal with soft waste items. Also, the decontamination treatment is not done until after the fragmenting.

The waste from a physician's or dentist's office and for which safe disposal is needed, includes not just hard items such as needles, syringes and vials, but also soft items such as bandage material and rubber gloves. It is desirable to avoid the necessity of sorting these things before disposal. The existing prior art equipment in a size suitable for portable, desk-top or counter-top use in a comparatively small facility, cannot suitably handle such a variety of materials.

Medical waste collection stations have been provided in hospitals, clinics, doctors' offices and other health agencies for the collection of medical waste as it is generated. Such medical waste collection stations have in the past included but a single container with a limited capacity for medical waste and have caused inconvenience and exposure to risk when a user, faced with a filled medical waste container, would be unable to dispose of medical waste, such as a used hypodermic needle, at the locale at which it was used. Under such circumstances, the user frequently had to carry the medical waste and used hypodermic needles to other remotely located medical waste containers, thereby exposing himself and others to the possibly infectious and toxic medical waste in violation of safety regulations.

A number of other problems attend the use of currently available medical waste collection stations. Overfilling of containers is a common problem and programs for the periodic replacement of medical waste containers frequently results in under-utilization of container capacity. With many wall-mounted collection stations it is difficult to determine the fill status of the container and to insert medical waste into the container.

SUMMARY OF THE INVENTION

The invention provides a method and apparatus for the collection and treatment of contaminated medical waste, including such solid items as syringes and needles, glassware, tubes, vials, culture plates and specimens, and disposable scalpels, and such soft and fibrous materials as gloves and masks. This invention permits the collection of such medical waste at the point and at the time of its generation in a container, which cannot be pierced or torn by the solid waste and in which the waste can be subsequently transported, pulverized and disinfected for easy disposal on site.

The invention eliminates repeated handling of the medical waste and the associated danger of the inadvertent transmission of infectious diseases resulting from the handling of such waste. The invention permits these substantial safeguards to be enjoyed by those personnel working in smaller doctor's and dentist's offices and smaller clinics, which often do not have access to proper medical waste processing facilities, without unnecessary expense and duplication of apparatus.

The apparatus of the invention provides a separate portable processing chamber, with an integral means to treat medical waste, that can be used at locations remote from its power unit for the collection of medical waste and then moved to the remote location of the power unit to drive the waste-treatment means within the chamber for pulverizing and disinfecting the medical waste within the chamber without danger to medical or operating personnel.

The apparatus of the invention comprises a separate waste collection and processing assembly including a closable chamber for the collection, pulverization and disinfection of medical waste. A rotating waste treatment system is rotatably carried within the chamber by bearings spaced on a supporting cylinder that is carried by the chamber bottom around a centrally located aperture through which the rotating system is driven. The rotating waste treatment system includes a plurality of pivotable blades that are carried by a rotating hub and have a configuration which, in cooperation with the chamber walls, provides effective disintegration, pulverization and blunting of solid waste and cutting and mincing of non-solid waste, and the circulation and disinfection of the medical waste within the separate chamber. An inner surface configuration of the chamber provides surfaces coacting with the rotating blades to destroy the waste material and effectively directs the waste during its destruction and disinfection. Furthermore, the separate chamber is self-cleaning and provides collection means from which the destroyed and disinfected waste material may be easily poured.

In preferred systems of the invention, an imperforable but breakable container is adapted to receive and contain used and possibly infectious solid waste, such as hypodermic needles, at a site of their use and thereafter permits their safe handling in the container, and the apparatus is adapted to permit the insertion of imperforable but breakable containers into its chamber carrying the used hypodermic needles, and for the destruction and disinfection of the breakable container and the used hypodermic needles that is safely contained while outside of the chamber.

One embodiment of the apparatus of the invention further includes rigid fenders carried by the rotating waste treatment system in front of the pivotable blades and extending downwardly to a small clearance from the chamber bottom, to sweep soft waste from adjacent the rotating hub and prevent it from collecting and being carried under the rotating hub. The fenders can be raked in the direction of rotation and provide blade impingement surfaces to prevent the blades from pivoting forwardly in the direction of rotation past a radial line extending outwardly from their pivotal mountings. In addition, the fender-forming surfaces can extend upwardly on the rotating hub within the chamber to provide one or more rotating surfaces to fractionalize the breakable containers that carry used hypodermic needles and other solid waste.

A further embodiment of a rotating hub assembly of the apparatus of this invention includes a ring that extends outwardly from the rotating hub from its lower end to prevent soft waste from being carried under the hub. The rotating hub assembly can also be provided with a pair of slots formed in its outer surface in which the blades are pivotally attached. The slots are preferably formed by a blade impingement surface adjacent the pivotal blade mounting, and extend away from the blade impingement surface in the direction opposite the rotation of the hub so that the blades can pivot partially within the hub in response to stationary objects and are prevented from pivoting forwardly in the direction of rotation past their mountings by the forward blade impingement surface of the slot. The rotating hub assembly further includes tooth member, equipped with a metal or carbide tip, protruding upwardly and outwardly adjacent the top surface of the hub.

In addition, a radially extending surface can be provided in the waste treatment chamber sidewall which is positioned to direct waste material at the abutment bar for destruction by the coaction of the abutment bar surfaces and the pivotable blades of the rotating waste treatment assembly.

In the invention an alternative hub can be provided with an outer, generally frustoconical surface, an outwardly extending ring adjacent the lower edge of the hub member and curved fins extending outwardly from the opposite sides of the outer surface of the hub and from near the top of the hub to the lower ring. This alternative hub may be used to replace the rotating hub assembly and, in operation, effect the complete cleansing and disinfecting of the soft medical waste.

In preferred apparatus of the invention, the waste treatment chamber is closed by a removable filter cap carrying a high efficiency particulate air filter that permits the escape of air and water vapor from the chamber during the operation while trapping aerosols and fine particles.

Preferred apparatus can also include means for isolating the waste treatment chamber and its driving motor from their supporting enclosure. Such means can include a support plate to carry both the waste treatment chamber and the driving motor for the waste treatment assembly, a pair of isolating straps to carry the support plate from the enclosure and a plurality of vibration absorbing mounts for carrying the support plate on the isolating straps.

This invention further provides a multi-container medical waste collection station, that permits sequential access to and filling of multiple medical waste containers and provides notice when a medical waste container at a medical waste collection station is ready to be emptied. This embodiment of the invention provides first means for supporting a plurality of medical waste containers, each of which has an open top permitting the insertion of medical waste, and second means, carried by the first means, for sequentially providing access to the open tops of the medical waste containers, one after the other. Preferably, the second means comprises a movable element with a plurality of positions, each position of the movable element allowing access to the open top of one of the medical waste containers and preventing access to the open tops of the others. Furthermore, in preferable embodiments of the invention, the first means carries indicia and the second means is operatively associated with the indicia to provide notice when one or more of the medical waste containers is ready to be emptied.

A preferred medical waste collection station provided by this embodiment of the invention can comprise a station enclosure, as said first means, capable of supporting and enclosing at least two medical waste containers arranged side by side, with at least two waste containers being supported by the station enclosure with their open tops below and adjacent a top opening of the enclosure. The station enclosure carries a movable means or element, as said second means, adjacent its top opening for limiting access by user to the open top of the single medical waste container through the top opening of the station enclosure. The movable means is movably carried by the station enclosure to provide a plurality of positions with each position providing access to a different single waste container and otherwise blocking access to the remaining waste containers. The movable means is preferably a cover slidably carried by the station enclosure at its top opening and slidable between its plurality of positions, each position of the movable cover closing a portion of the top opening of the station enclosure except over the open top of a single waste container. In a preferred embodiment including two medical waste containers, the movable cover extends partially over the open top of the station enclosure, is engaged by a spring carried by the station enclosure and includes a latch portion extending downwardly from the movable cover. The movable cover is urged by the spring into a first position where it extends over one of the waste containers and exposes the open top of the other waste container and is movable to a second position where its latch portion is engaged, e.g. by a part of the first means or the top of the other container, to retain the movable cover in the second position and expose the open top of the one waste container. In this preferred embodiment, the station enclosure carries indicia exposed by the movable cover when the movable cover is in the second position.

In the invention the first means may be provided with a hypodermic needle-engaging surface adjacent the open top of one or more medical waste containers to engage a hypodermic needle and permit its disengagement from a syringe by a user and its insertion into an adjacent medical waste container without handling by the user.

Other features and advantages of the disclosed embodiments and methods of the invention will be apparent from the drawings and more detailed description of the invention that follows.

BRIEF DESCRIPTION OF THE DRAWINGS

FIGS. 18A and 18B are schematic side views illustrating how the medical waste collection station of FIG. 15 may be opened to gain access to the medical waste containers carried therein;

FIG. 21 is an enlarged partial side cross section of the upper portion of a medical waste collection station of the invention showing an alternative means by which the slidable cover can be secured.

DESCRIPTION OF THE PREFERRED EMBODIMENT

Figure 1:
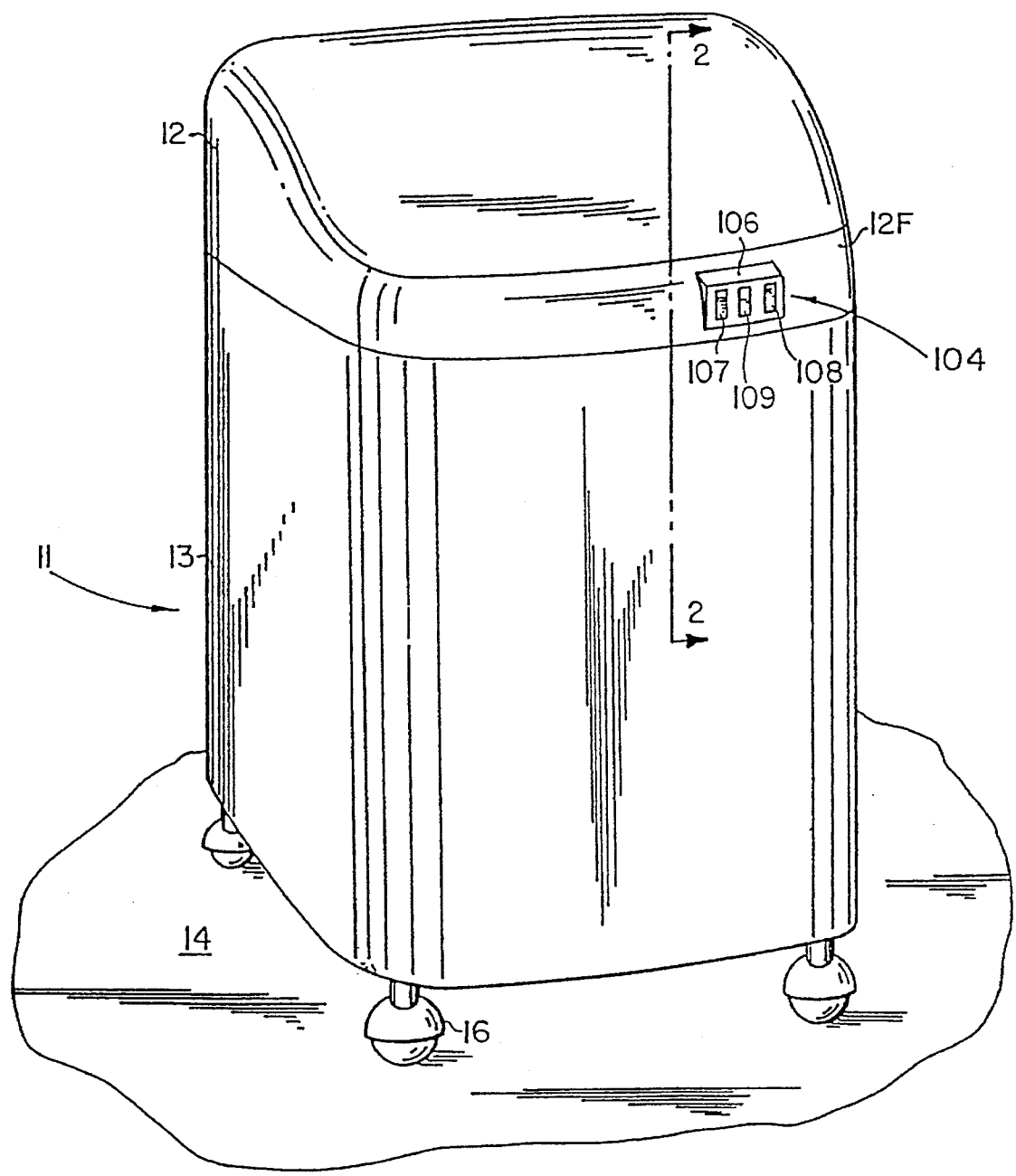
FIG. 1 is a pictorial view of a portable waste treatment device according to the invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 3:
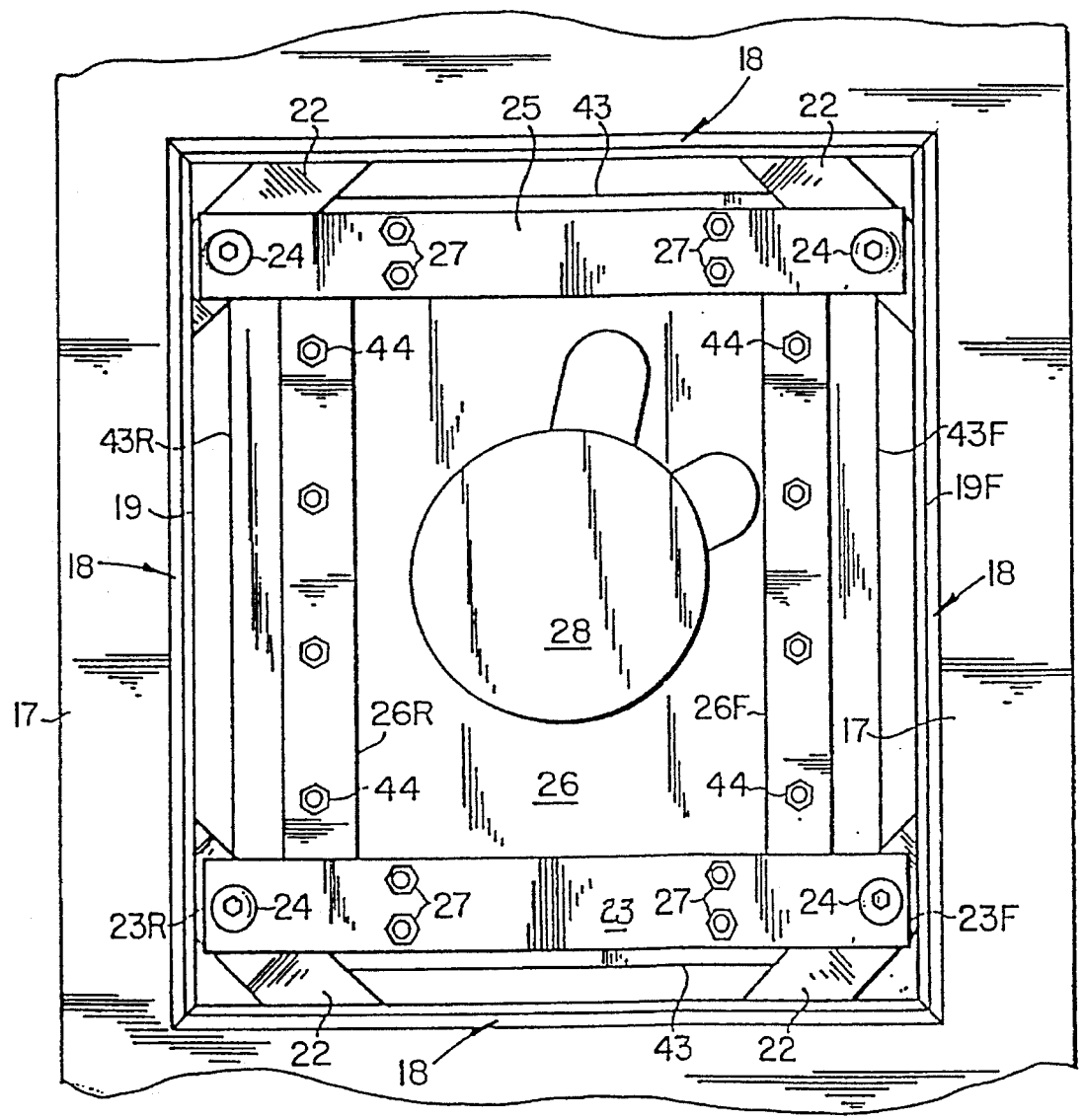
FIG. 3 is a fragmentary section taken at line 3—3 in FIG. 2 and viewed in the direction of the arrows.
Figure 4:
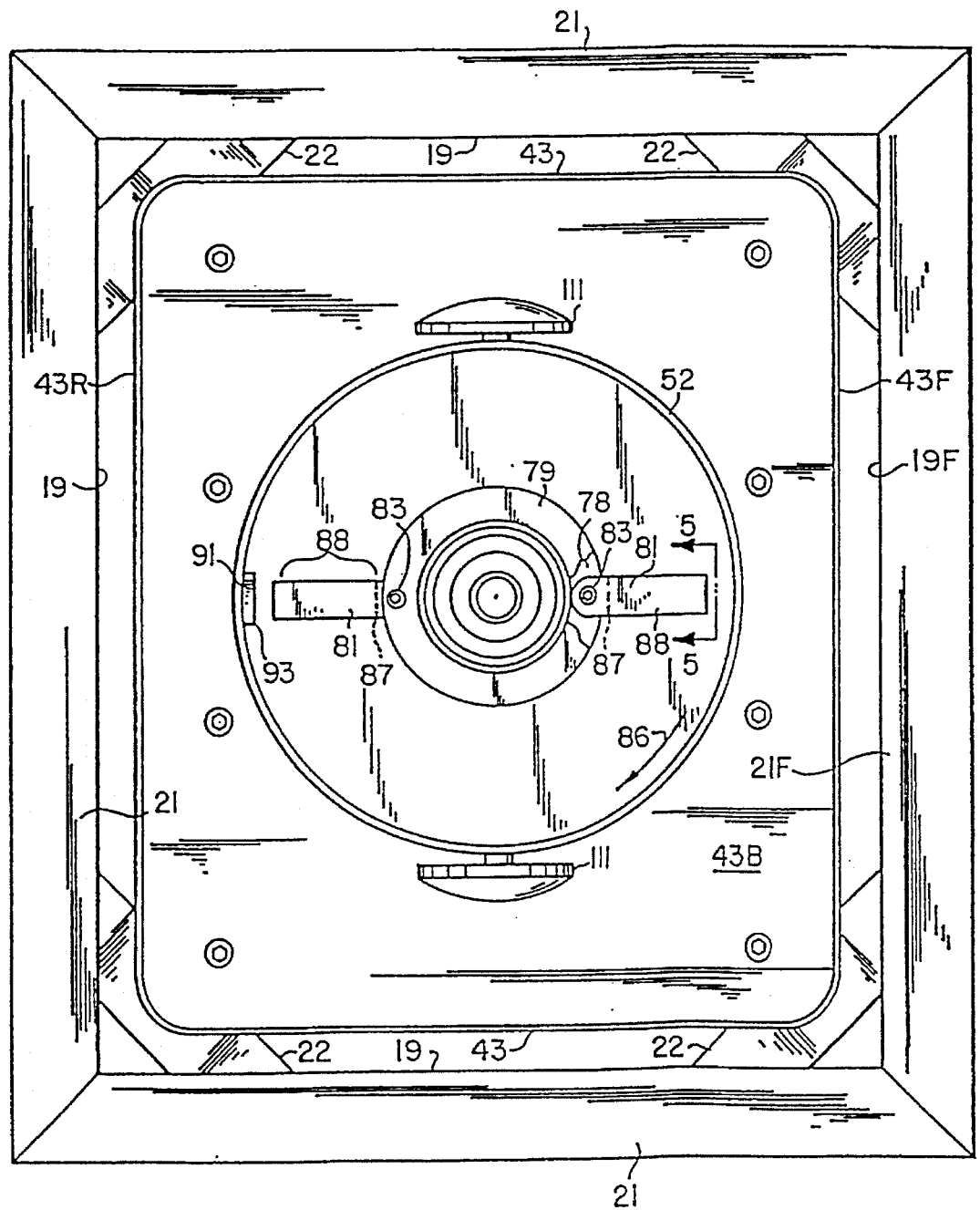
FIG. 4 is a section taken at line 4—4 in FIG. 2 and viewed in the direction of the arrows.

Referring now to the drawings in detail, and particularly FIG. 1, a floor-mounted, mobile unit 11 includes a main cabinet 12 mounted on the top of a cart 13 which is movable along the floor 14, being supported on four casters 16, one at each corner. Referring now to FIG. 3, and regardless of whether a mobile cart 13 or a stationary counter top is the site for the present invention, it will include a support 17 which, in the illustrated embodiment, is rectangular in shape, framing a central opening 18 in which the waste treatment device is mounted according to the present invention. For this purpose, a rectangular frame 19, typically metal, is provided with an outwardly extending perimetrical flange 21 (FIGS. 2 and 4) and is mounted on the support 17 and may be secured to it in any suitable manner. The portions of frame 19 and flange 21 that are at the front of the machine are designated 19F and 21F. Frame 19 has a gusset 22 welded to it at each of the four corners of the frame. An isolation strap 23 having a front end 23F and rear end 23R is mounted to the frame gussets 22 at their respective ends by means of isolator couplings 24. An identical strap 25 and mounting arrangement is provided at the opposite side of the frame 19.

A motor mount plate 26 is mounted on top of the two straps, with four fasteners 27 securing each side of the plate to each of the two straps 23 and 25. In the illustrated example, the fasteners are socket head cap screws with nuts. This motor mount plate is generally U-shaped as shown best in FIG. 2. The motor 28, having a standard C-face 29, is fastened to the bottom center of the plate 26 by four socket head cap screws 31. The motor shaft 32 extends up through a central aperture 33 in plate 26 and is provided with a slinger ring 34 immediately above the plate 26. The motor shaft has a standard square keyway to receive a standard square key 37 in coupling 38 to which the key is secured by set screw 39. The upper end of the coupling 38 is provided with a ½ inch square cross section at 41.

The outwardly turned front and rear flanges 26F and 26R, respectively, of the motor mount plate support the main cabinet 12. The cabinet has a front wall 12F, and a rear wall 12R and is molded in one piece of fiberglass reinforced plastic with a generally centralized tub portion 42 which is generally rectangular in configuration as shown by the front and rear walls 43F and 43R, respectively, and the sidewalls 43 in FIG. 4. The floor 43B of the tub is secured to the outwardly extending flanges 26F and 26R of the motor mounting plate by four fasteners 44 through each of the flanges, these fasteners typically being socket head cap screw and nut assemblies.

A hollow bulb gasket 46 is secured to the inside of the cabinet outer shell around the entire perimeter of the lower edge 47 of the shell. This gasket 46 lightly but sealingly engages the top surface of the support 17 entirely around the perimeter of the cabinet. However, it does not provide support for the cabinet since that is supported by the motor mount plate supporting the bottom 43B of the cabinet tub portion.

The flask assembly 51 of the present invention includes a flask lower housing 52 and flask top housing 53, both of which are symmetrical about the central axis 54. The flask lower housing has an outwardly turned upper circular flange 52U supporting an O-ring 56 which supports the circular bead at the bottom of the flask top housing. The top and lower housings are fastened together by over-center lever operated spring clamps 57 such as are available from Dzus Fasteners of West Islip, N.Y. 11795. The bottom of the flask lower housing has four circularly spaced feet 58 which are received in sockets 59 in the floor 43B of the cabinet tub portion. These feet support the flask assembly in the cabinet tub. They also prevent the flask assembly from rotating in the tub.

Figure 5:
FIG. 5 is an end view of a blade taken at line 5—5 in FIG. 4 and viewed in the direction of the arrows.

An impeller assembly 61 is mounted in the flask assembly. It is located and supported by a bearing mount cylinder 62 which is welded to the bottom of the flask lower housing at 63 around the central opening 64 in the flask bottom. This bearing mount cylinder receives the lower ball bearing assembly 66 and the upper ball bearing assembly 67. The inner race of each of these ball bearing assemblies fittingly receives outer cylindrical surfaces of the impeller shaft 68 which has an octagonal internal spline or socket at 69 received on the square upper end of the coupler 38. The upper portion of the impeller shaft has a sleeve 71 pressed thereon above the inner race of the upper bearing 67. This serves to engage a lip seal 72 which is secured in the outer race receiving bore of the impeller bearing mount cylinder 62. The upper end of shaft 68 is threaded at 73 and threadedly receives thereon the top 74 of the impeller which extends from the top down to the slinger flange 76 at the bottom and which is immediately above the bottom of the flask lower housing. The cylindrical wall 77 of the impeller has two additional circular flanges above the slinger flange 76. These are the blade support flange 78 and the blade hub cover flange 79. Two blades 81 are mounted in the annular groove 82 between the flanges 78 and 79 and pivotally secured in place by the pins 83 which are shoulder bolts screwed into the flange 78. The shape of these blades can be observed in FIG. 4 and FIG. 5. The blades are driven in the clockwise direction of arrow 86 in FIG. 4. Although the hub area of the blade is rectangular as shown in FIG. 5, the blade is tapered beginning at a line 87 (FIG. 4) to provide a sharp leading edge 88 while the trailing edge of the blade 89 is the full height of the hub portion. The blade is made of a tungsten carbide compound.

A "baffle" bar 91 is mounted on the inside upstanding cylindrical wall of the flask lower housing and extends up from near the bottom to a top edge 92. Thus, it presents a 90° angle edge 93 facing the materials as they are driven around by the impeller blades moving in the clockwise direction of arrow 86. Due to the inclination of the lower face of the blades 81 downward from the front or leading edge toward the rear or trailing edge, as the blades 81 rotate the trailing edge of each is closer to the bottom of the flask than is the sharp leading edge. This drives the waste materials downward and thus assures that they will be aggressively treated by the baffle bar 91 during operation.

A removable flask cap 96 is provided in the central opening 97 at the top of the frustoconical surface of the flasktop housing. This cap 96 has a tapered wall 98 so as to be manually insertable to the point of a snug fit, but can be readily removed manually, if desired, by means of the outwardly directed circular flange 99 at the top of the cap. The cabinet is provided with a lid 101 which is hinged to the upper rear wall 12R of the cabinet by adjustable hinges 102 such as the 500 Series marketed by Southco, Inc. of Concordville, Pa. 19331. These hinges are adjustable so that the lid can be raised at the front end edge in the direction of arrow 102a and can remain in virtually any position up to vertical. The underside of the lid has an inwardly projecting bulge 103 therein which, when the lid is closed, engages the flask cap 96 and assures that the cap will remain securely closed in place on the flask top housing. A bulb gasket may be provided around the perimeter of the cabinet lid to seal against the cabinet top during operation.

Figure 6:
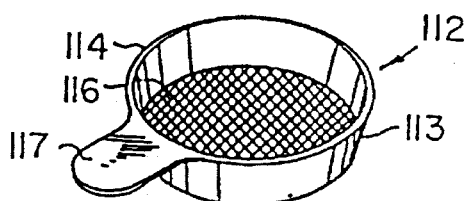
FIG. 6 is a perspective view of a strainer plug used in the practice of the invention.

Referring to FIG. 6, a strainer cap 112 is shown. It is similar to cap 96, having a tapered wall 113 and perimetrical top flange 114 but, instead of a solid bottom, the bottom 116 is a screen. It may also have a handle tab 117 at the top flange.

Referring again to FIGS. 1 and 2, a control group 104 is provided on a boss 106 at the front of the cabinet and includes a momentary contact "ON" switch 107, and "EMERGENCY STOP" switch 108, and a pilot light 109 illuminated when the operating cycle is in progress. These are associated with suitable electrical circuitry to control the motor as desired. The circuitry is not shown herein as it may be conventional and well within the skill of the art.

Referring again to FIG. 4, a pair of T-type handles 111 may be provided on the side of the flask lower housing for a purpose which will be described now.

OPERATION

The flask assembly is removable from the main cabinet by simply lifting the cabinet lid and lifting the flask assembly out of the cabinet by use of the T-handles, one in each hand. The flask assembly can be easily lifted off the coupler and moved to whatever site location is convenient for deposit of medical waste material into it, wherever such material is being generated. Of course, if the unit is mounted on a moveable cart as in FIG. 1, the cart can be simply pushed to the site without removing the flask assembly from it. With the top cap 96 pulled out of the top of the flask assembly, the waste material can be simply dropped into the flask assembly through the to opening 97. The opening is large enough in diameter, four inches, for example, to readily receive syringes, bandage material, rubber gloves, culture plates and vials, for example. Such waste materials can be dropped directly into the opening as they are produced, rather than putting them in another container and then transferring them later to the flask. For example, as a bandage is removed from a subject, the bandage materials are placed directly into the flask. When the flask assembly has been filled to a level about even with the top of the flask lower housing or bowl 52, and if the flask assembly is separate from the main cabinet, it can then be returned to the main cabinet and placed on the cabinet tub bottom with the four feet 58 in the pockets 59. Simultaneously the impeller shaft socket is received on the coupler square 41. Water is then poured through the top opening 97, a pouch of decontaminant is added, and the top cap 96 is installed and the cabinet lid is closed. The start switch 107 is then pushed past the lid and may thereupon be locked by an automatic electrically operated lid latch (not shown). The motor is energized and drives the impeller and, the blades are driven thereby in a circular path, clockwise as per arrow 86 in FIG. 4 around the impeller axis. As the blades are driven, they begin to cut-up the waste material in the housing. Although the materials provide some resistance to the blade action, the combined effects of the sharp leading edges 88 of the blades, and the centrifugal force, keep them deployed in a radially outward extending direction to continue to cut up the waste material. As this occurs, the slinger flange 76 at the bottom of the impeller assembly keeps the material moving outward and upward around the curved outer portion 55 of the flask lower housing wall 52. Thus, the material is kept moving in a path outward and upward along the wall and then back down into the path of the blades. Also, the presence of the vertical block (baffle) 91 provides an abutment which, to materials moving in the clockwise direction, is relatively sharp. In addition, baffle 91 inhibits the free circular flow of material around the inner wall of the flask lower housing, tending to direct it back into the path of the blades. The baffle 91 facilitates destruction of sharp items and facilitates cutting of soft materials. This processing continues as long as desired until it is either stopped by expiration of the "run" period of an automatic timer, or is manually stopped by pushing the emergency stop pad 108 to simply end the desired cycle. The pilot light serves as an indicator that a cycle is in process. This light may remain on for several minutes after the processing is complete in order to indicate to the operator that it is not yet time to open the lid, because the contents have not yet settled.

When the pilot light goes out, the operator can then open the lid, grip the T-handles, pull the flask assembly out of the tub of the main cabinet, and take it to a sink. The cap 96 is removed and replaced by the strainer 112 in the opening 97. Then the flask assembly is inverted in the sink, and the decontaminant solution, together with any other liquids which were contained in the waste material are drained into the sink. Then the flask assembly is righted and moved over to a solid waste receiver bucket or bag or the like, and the processed waste materials are dumped into the receiver for later disposal in a conventional waste container.

As an alternative procedure, instead of using the strainer, the flask assembly can be dumped, liquids and solids simultaneously, into a disposable bag containing a liquid-absorbent gel compound. Then the flask is righted and ready for return to the waste generation site for collection of more waste in it.

With a machine built according to the present invention, in addition to the mincing action on materials, needles are bent and blunted as they are driven into the baffle 91. If it is ever desired to do so, the flask can be washed out without taking it apart, just as one could wash out a vase or bowl. If ever desired, such as for servicing interior components, the flask upper and lower housing can be separated by releasing the spring clamps 57. After servicing, they can be re-assembled, clamped together, and the flask assembly can be returned to the waste generation site for use again as described above.

As an example, the chamber forming flask components can be made of spun stainless steel. Many of the more dense components, such as the impeller bearing mount cylinder, the impeller shaft, and the impeller itself, can be stainless steel investment castings. For a flask assembly that will hold and process approximately one-two gallons of medical waste materials in their final processed state, a drive motor of two horsepower is useful to complete a processing of that much material within a two to three minute cycle. A rotational speed of about 3450 r.p.m. is advisable for effective destruction of the solid and soft medical waste identified above. Examples of suitable decontaminant solutions are a one ounce package of A-33 dry decontaminant powder as marketed by Airkem Professional Products of St. Paul, Minn. and an Iodophor disinfectant compound sold by Ecolab, Inc. at Minneapolis, Minn. under their trade name "Mikroklene". Dumping of treated waste from the flask can be into a plastic bag of appropriate size and at least three mil membrane, and preferably an eight gallon, double ply plastic bag, which contains a polymeric absorbent powder which develops a gel as it absorbs the liquid. The bag preferably has a drawstring for convenient handling and can be placed in a conventional trash or garbage container. Although the description refers to a one-gallon flask or chamber, it should be appreciated that the present invention can be applied to larger or smaller size apparatus.

Figure 7:
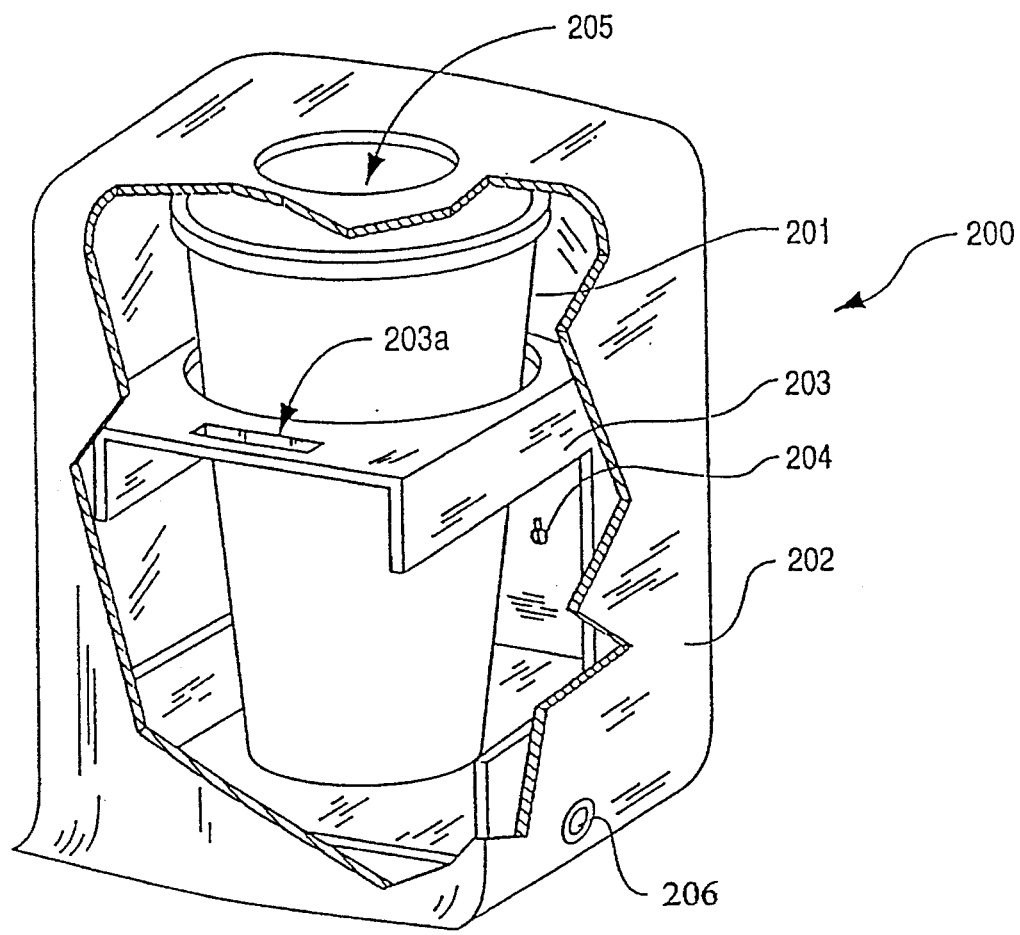
FIG. 7 is a partially broken away perspective view of a collection station for medical waste such as used and possibly infectious hypodermic needles.
Figure 7A:
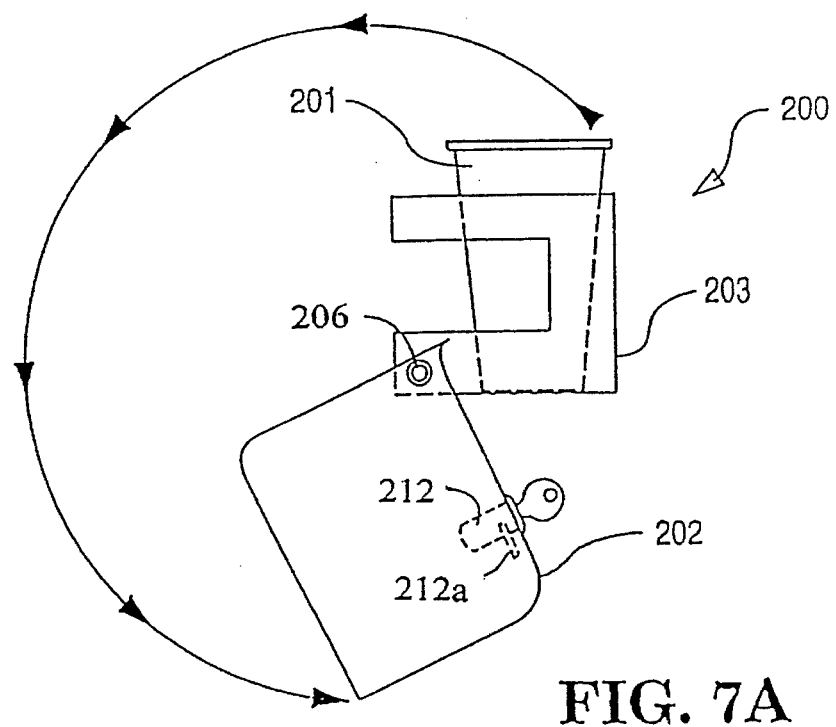
FIG. 7A is a diagrammatic drawing of an open collection station.

Preferred systems of the invention can include the use of an imperforable but breakable container, which is particularly adapted to receive and contain used and possibly infectious, sharp solid waste, such as used hypodermic needles. Such a container, or containers, may be located at the locations in which blood samples are taken or injections are given for the collection of the possibly infectious used hypodermic needles. FIG. 7 is a partially broken away perspective drawing showing a collection station 200 for used hypodermic needles that includes such an imperforable but breakable container 201. As shown in FIG. 7, the collection station can comprise a lockable housing 202 including an inner mounting bracket or plate 203 adapted to be fastened to the wall, for example, by a plurality of screws 204. The hinged cover 202 includes an orifice 205 permitting medical personnel to insert used hypodermic needles and other medical waste into the container 201. The lockable housing 202 comprises a hinged lockable cover (partially broken away in FIG. 7) which may be pivotally carried by hinges 206 and locked by a lock 212 to the inner mounting bracket to prevent access to the collected medical waste. The keyed cylinder and locking bar of the lock are in the portion that is broken away from housing 202 in FIG. 7, but the opening 203a is engaged by the locking bar 212a of the lock 212 which is shown in FIG. 7A. Access to the materials in the collection station can be thus limited to authorized personnel. The hinge cover 202 may be unlocked by authorized personnel and swung downwardly to the position indicated in FIG. 7A, thereby permitting the removal of the imperforable but breakable container 201 from the inner mounting bracket 203 which supports it within the collection station 200.

Container 201 for used medical waste, such as hypodermic needles, is preferably formed or molded from a material which cannot be perforated by such sharp, solid waste as used hypodermic needles but which will break or fractionate or shatter when impacted. A preferable such material is clear molded polystyrene of the type commonly used for inexpensive drinking utensils. The container 201 may be molded in a glass or cup-like shape as shown in FIG. 7, with thin walls on the order of about 1/32 to about 1/16 inch thick to provide safety in handling of its contents after collection at the collection station 200. Preferably, a molded polystyrene cover with downwardly turned lip adapted to snap fit over the open top of the container 201 can provide the container 201 with an imperforable but breakable cover (indicated at 201a on FIG. 9) for the further safe handling of the container's contents after its collection. A screw-on lid that can be threadably secured to the container may also be used. While clear polystyrene is a preferable material for container 201 because of its low cost, transparency, imperforability and its desirable degree of breakability, other materials, such as glass, may also be used for container 201.

Where the description above refers to used hypodermic needles, it should be recognized that not only the needle portion but the entire syringe may be collected in container 201 for safe disposal. In addition, disposable scalpels and other sharp solid medical waste and even soft medical waste may be collected at collection station 200 in container 201 for safe handling.

Figure 2:
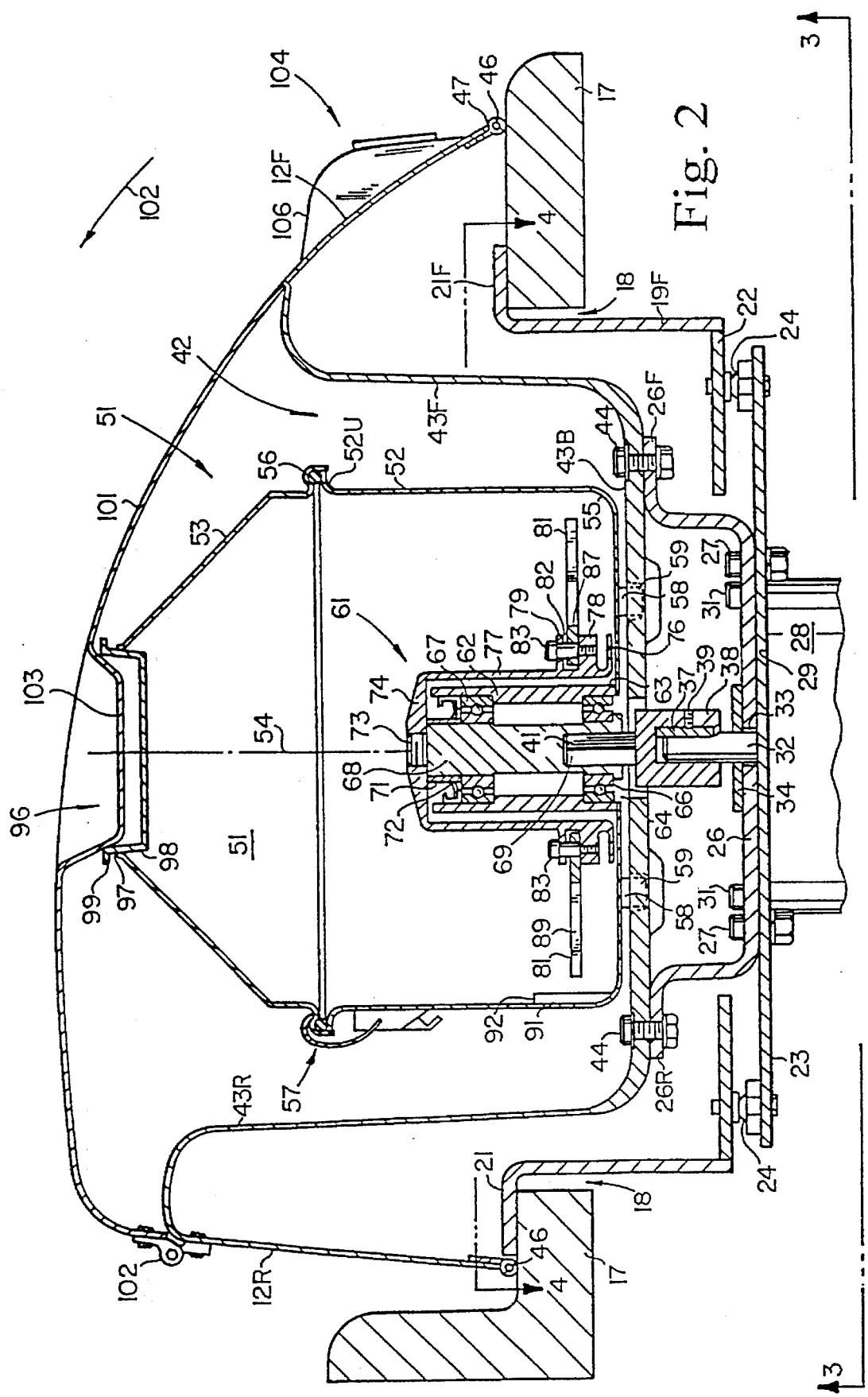
FIG. 2 is an enlarged fragmentary vertical section through a portion of the cabinet taken at line 2—2 in FIG. 1 and viewed in the direction of the arrows and showing some interior details.
Figure 8:
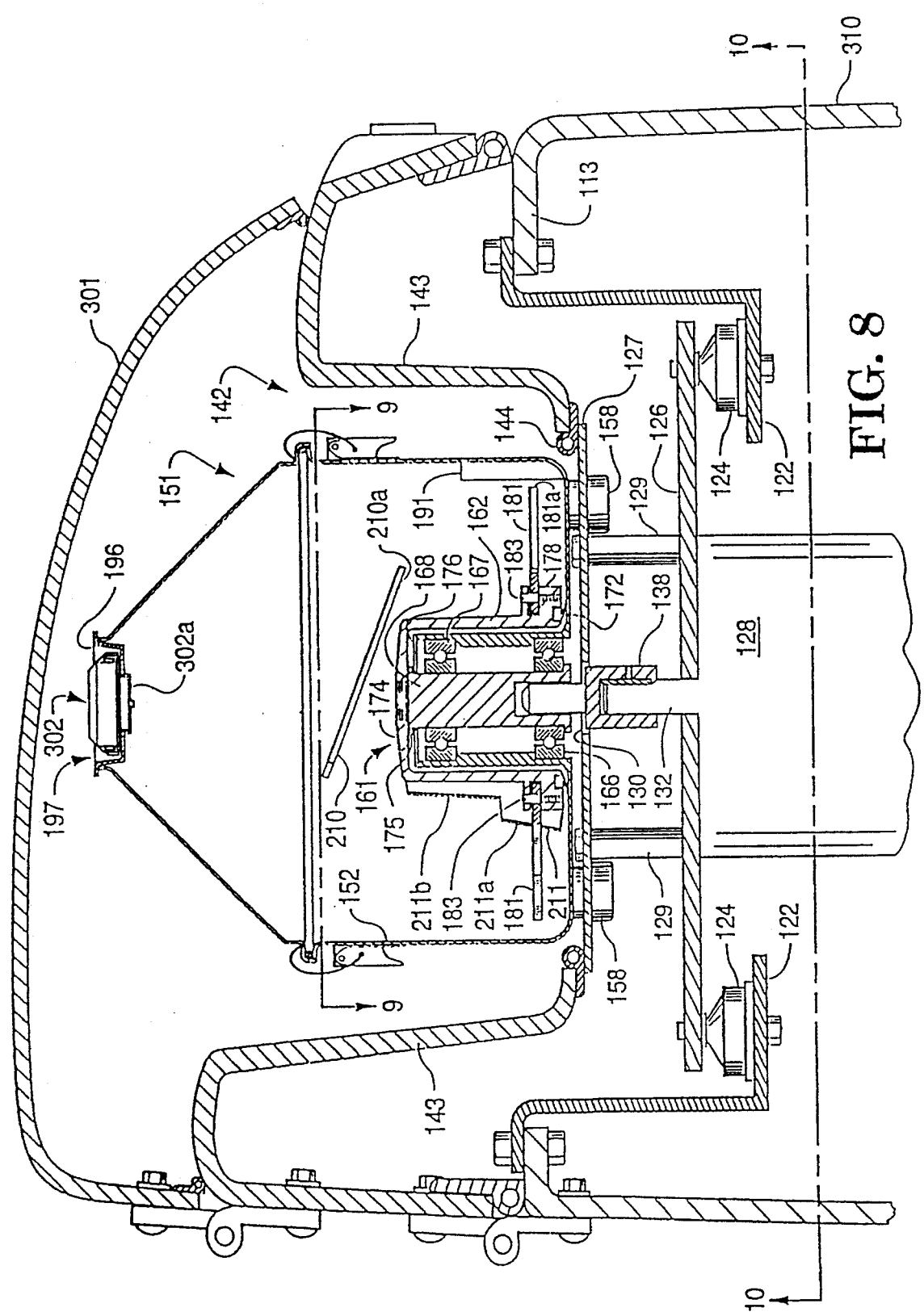
FIG. 8 is a cross-sectional view of a further preferred embodiment of the invention, taken at a central plane through apparatus at line 2—2 in FIG. 1.

Following the collection of solid medical waste in container 201, the entire container may be carried to and inserted in the waste treatment chamber of the type shown in FIGS. 2 and 8 for disposal. The container 201 carrying the solid medical waste may be inserted through the opening to the chamber (97 in FIG. 2 and 197 in FIG. 8) for destruction. As indicated in phantom lines in FIG. 9, container 201 will be impacted by one of the rotating surfaces of the rotating assembly within the chamber and will be shattered or fractionated, spilling its contents into the interior of the waste destruction chamber. In the chamber, used hypodermic needles and syringes and the pieces of the container 201 will be driven around the chamber being impacted by the pivotable blades 81, 181, and impacting the abutment surfaces of the abutment bars 91, 191, thereby breaking the larger pieces to small minced solid waste, bunting the tips and sharp edges of the needles, syringes, scalpels and the like, and scrubbing the surfaces of the waste materials with disinfectant.

Figure 9:
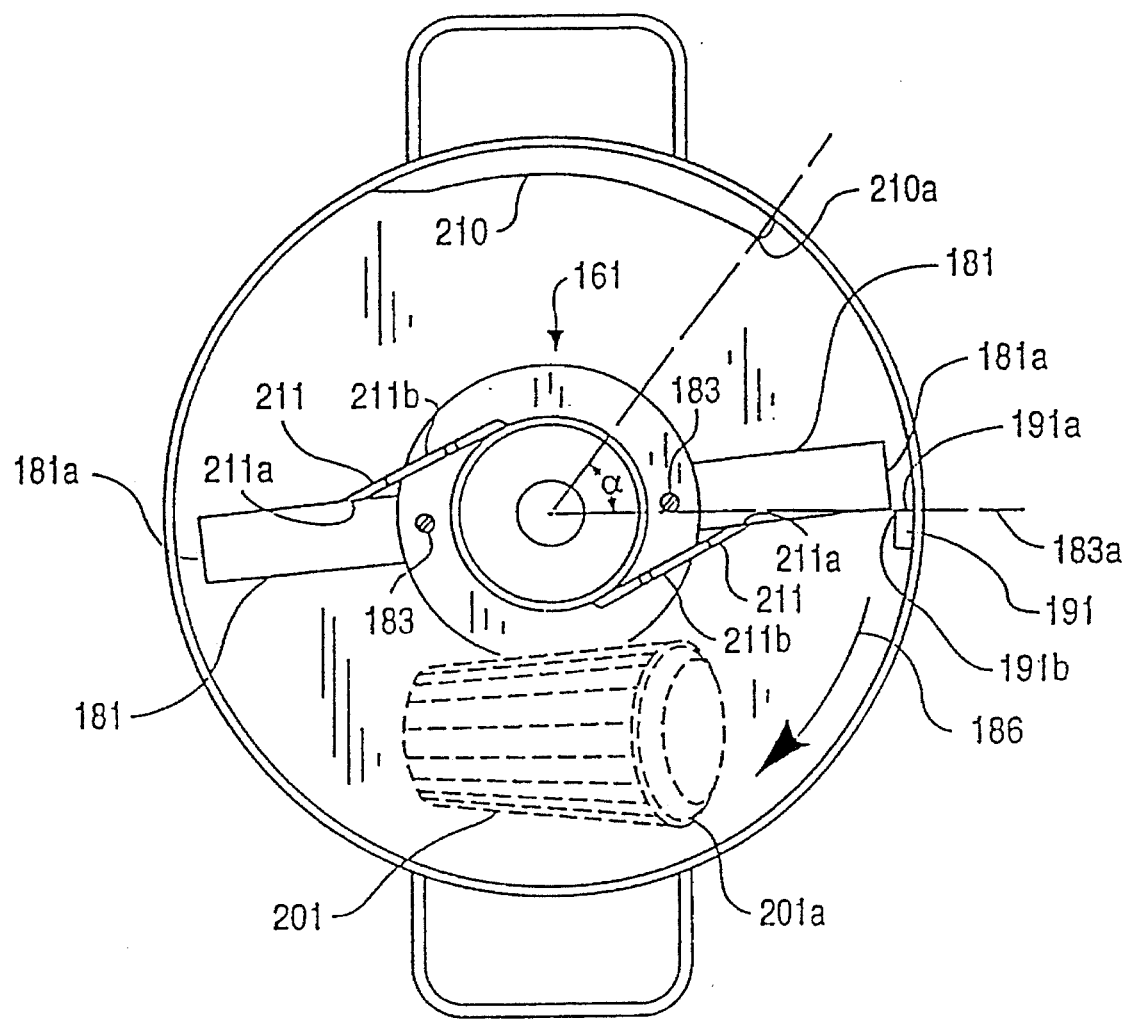
FIG. 9 is a view looking downwardly into the apparatus of FIG. 8 at line 9—9 of FIG. 8, showing in phantom lines a breakable container for the collection of medical waste.

FIG. 8 is a cross-sectional view of another embodiment of the waste treatment apparatus of the invention and FIG. 9 is a view downwardly into the interior of the medical waste treatment chamber of the FIG. 8 apparatus.

The apparatus of FIGS. 8 and 9 is in most respects identical to that shown and described above. Unlike the apparatus shown in FIG. 2, however, the underside of the hinged lid 301 of the apparatus shown in FIG. 8 does not include an inwardly projecting bulge, like bulge 103 in the apparatus of FIG. 2 which engages the flask closure 96 to ensure that the closure 96 would remain in place in the chamber opening.

Figure 10:
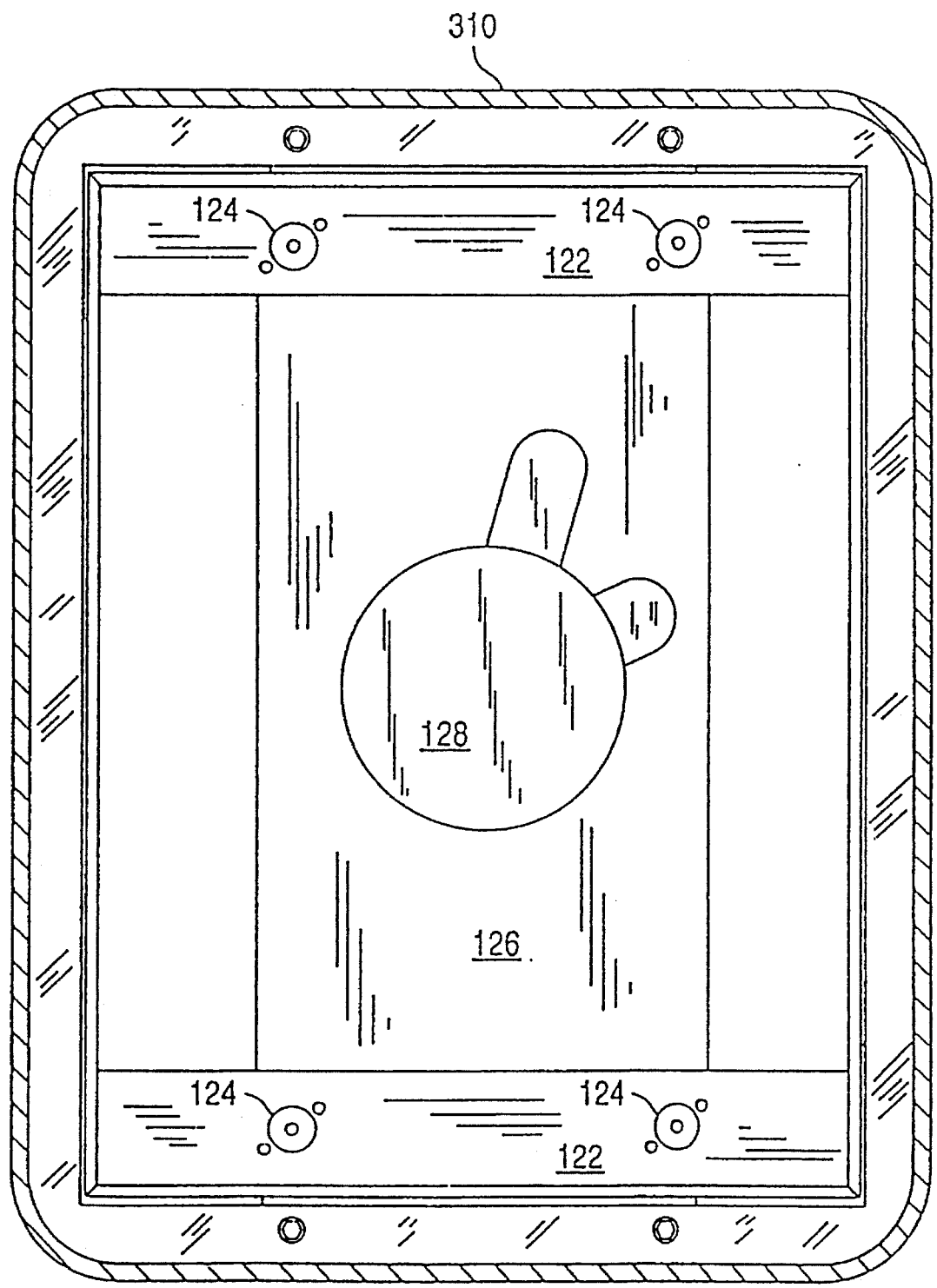
FIG. 10 is a cross-sectional view taken at line 10—10 of FIG. 8 and viewed in the direction of the arrows.
Figure 11:
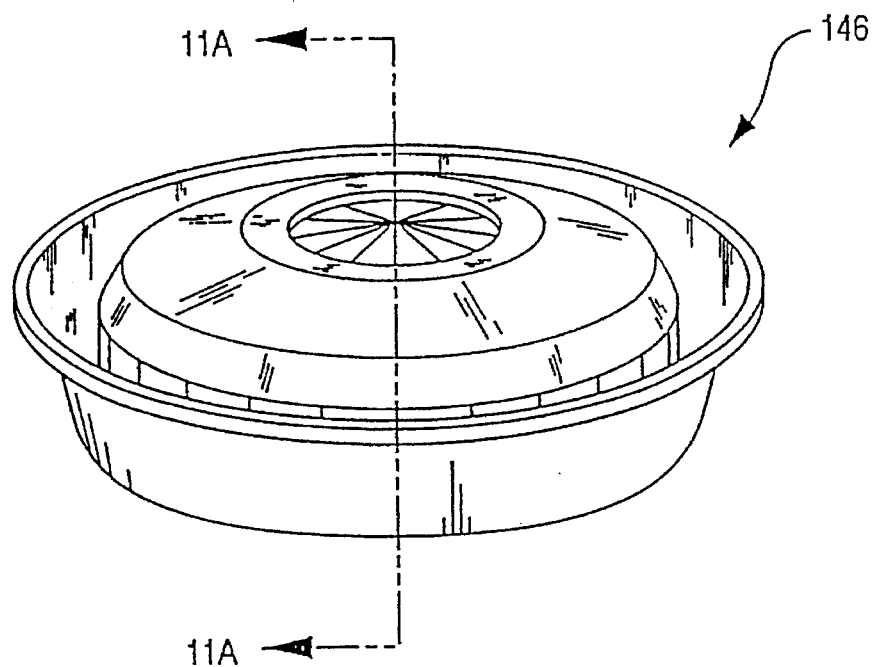
FIG. 11 is a perspective view of the waste treatment chamber closure.
Figure 11A:
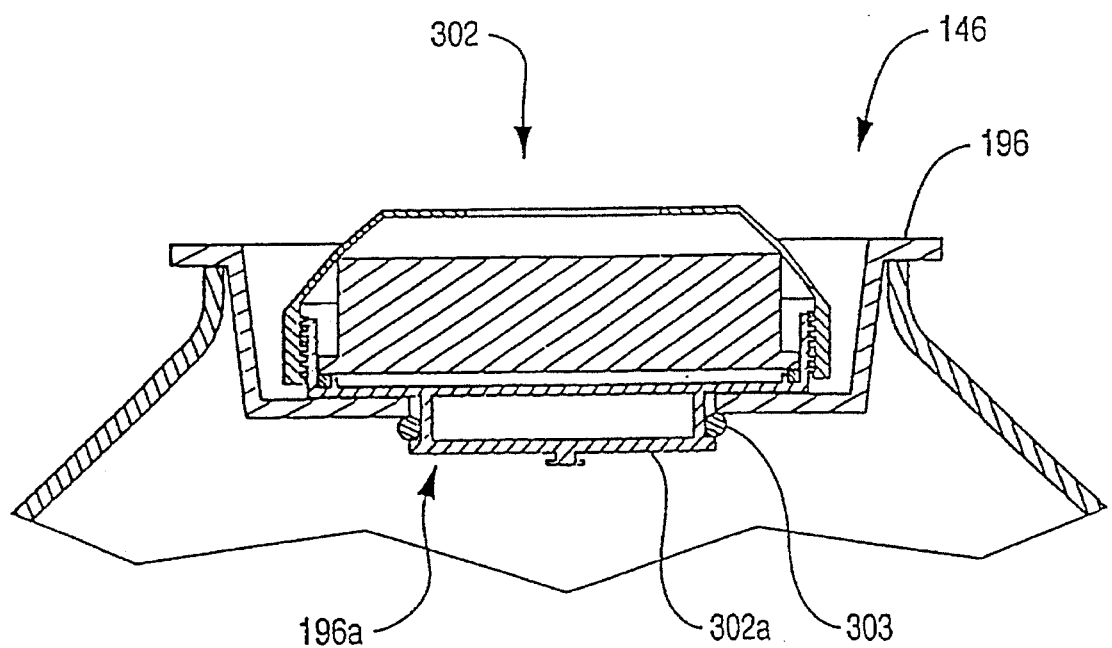
FIG. 11A is a cross-section of the waste treatment chamber closure taken at line 11A—11A of FIG. 11 and in the direction of the arrows.

In the apparatus of FIGS. 8–11, the closable chamber opening 197 is closed by a removable filter cap 196, as shown in greater detail in FIGS. 11 and 11A. Removable filter cap 196 carries a high-efficiency particulate air filter 302 of the type sold by the 3M Company as their filter Number 7255. The particulate air filter 302 is fitted to an opening 196a in the removable filter cap 196, which is otherwise identical to the cap 96 shown in FIG. 2. The particulate air filter 302 extends downwardly through the opening 196a formed in the base of cap 196 and is held in the cap by an O-ring 303 fitted over the filter portion 302a, which not only holds filter 302 to cap 196 but also seals the interface between the filter 302 and the cap 196. The O-ring retention of particulate air filter 302 thus permits an inexpensive method of fastening and sealing the particulate air filter 302 to the cap 196 and its simple replacement, if necessary. Particulate air filter 302 permits the passage of air and water vapor from the chamber during operation of the waste treatment apparatus but prevents aerosols and fine particles from escaping. Heat generated by the waste treatment within the chamber creates an expansion of the air and water vapor within the chamber which would tend to dislodge cap 196 from opening 197 in the absence of the particulate air filter 302.

As shown in FIGS. 8 and 9, a preferred apparatus of the invention includes a radially extending surface 210 on the chamber sidewall 152. Surface 210 is positioned to direct medical waste materials moving within the chamber to expose it to the coaction of the abutment bar 191 and pivotal blades 181. As shown in FIGS. 8 and 9, the radially extending surface 210 is preferably a ribbon of stainless steel having a thickness on the order of about 3/16 to about 3/8 of an inch and welded (or otherwise fastened) to the sidewall 152 of the chamber in a downwardly extending direction from adjacent the upper portion of sidewall 152 to adjacent the central portion of chamber sidewall 152 so that waste materials will, for example, leave the terminal portion 210a with the velocity directed at abutment bar 191. As indicated above and shown in FIG. 9, abutment bar 191 provides an abutment surface 191a extending radially inwardly from the container sidewall 152 against which the rotating waste materials impinge. Abutment bar 191 further provides a cutting edge at corner 191b which is located only a small clearance distance from the ends 181a of the blades 181, as indicated in FIGS. 8 and 9. The coaction of blade ends 181a, the abutment surface 191a and cutting edge 191b of abutment bar 191 cut and tear soft medical waste material, such as those described above, into small pieces, and fractionate and dull solid medical waste of the type described above into a generally minced condition. It will be noted that the radially extending surface 210 tends to direct materials adjacent the abutment bar 191 for exposure to this coaction. In preferred embodiments of the invention, the terminal portion 210a of the material deflector 210 is located "upstream" of the abutment surface 191a and cutting edge 191b, and the included angle α between its termination 210a and the surface 191a of the abutment bar lies in the range of 40°–90° to avoid entrapment and lodging of the waste material therebetween.

The apparatus shown in FIGS. 8 and 9 further includes a pair of fenders 211 (only one of which is shown in FIG. 8) affixed to the rotatable hub 161 adjacent the pivotable mountings 183 for the waste treating blades 181 and extending downwardly below the blade support flange 178 to a small clearance above the chamber bottom. The fenders 211 thus prevent soft medical waste material, such as cloth and plastic dressings and rubber gloves, from collecting under the blade supporting flange 178 where they may slow the rotation of the rotating hub 161 and rob the rotating waste treatment assembly of power. Fenders 211 sweep such waste material outwardly and impel it against the container sidewalls 152 for impingement by the abutment bar 191 and pivotable blades 181 and destruction thereby.

As shown in FIG. 9, placement of the rigid fenders 211 adjacent the pivotable mountings 183 of the waste treating blades 181 can provide surfaces 211a that impede the rotation of the waste treating blades 181 in the direction of rotation, as shown by arrow 186, forwardly of a radial line 183a extending outwardly from their pivotal mountings 183. If the pivotable blades 181 pivot in the direction of rotation in a direction forwardly of a radial line 183a from the center of the rotating head 161 through their pivotable mountings 183, the blades will tend to draw waste material toward the center of the chamber.

As shown in FIG. 9, the fenders 211 are raked to form a forwardly facing acute angle adjacent the blade supporting hub 178 to reduce drag and assist the action of fenders 211 in sweeping waste material toward the sidewalls 152 of the chamber and the abutment bar 191.

As further shown in FIGS. 8 and 9, fenders 211 may be formed by a pair of metal members that extend upwardly along the rotating hub 161 into the central portion of the chamber to provide an upper rotating edge 211b. The rotating edge 211b can be adapted to fractionalize larger breakable containers 201 which may be inserted within the waste treatment chamber.

As shown in FIG. 8, the rotating hub assembly 161 includes a seal-carrying groove formed in the lower surface of the rotating blade flange 178 and carries a rotating lip seal 172 between the bottom of the rotating blade hub portion 178 and the bottom of the chamber-forming flask assembly 151. The rotating V-ring seal 172 in cooperation with a V-ring seal 175 compressed between the top 174 of the impeller hub and a bearing protection plate 176 protect bearings 166 and 167 from chamber contents.

Figure 12:
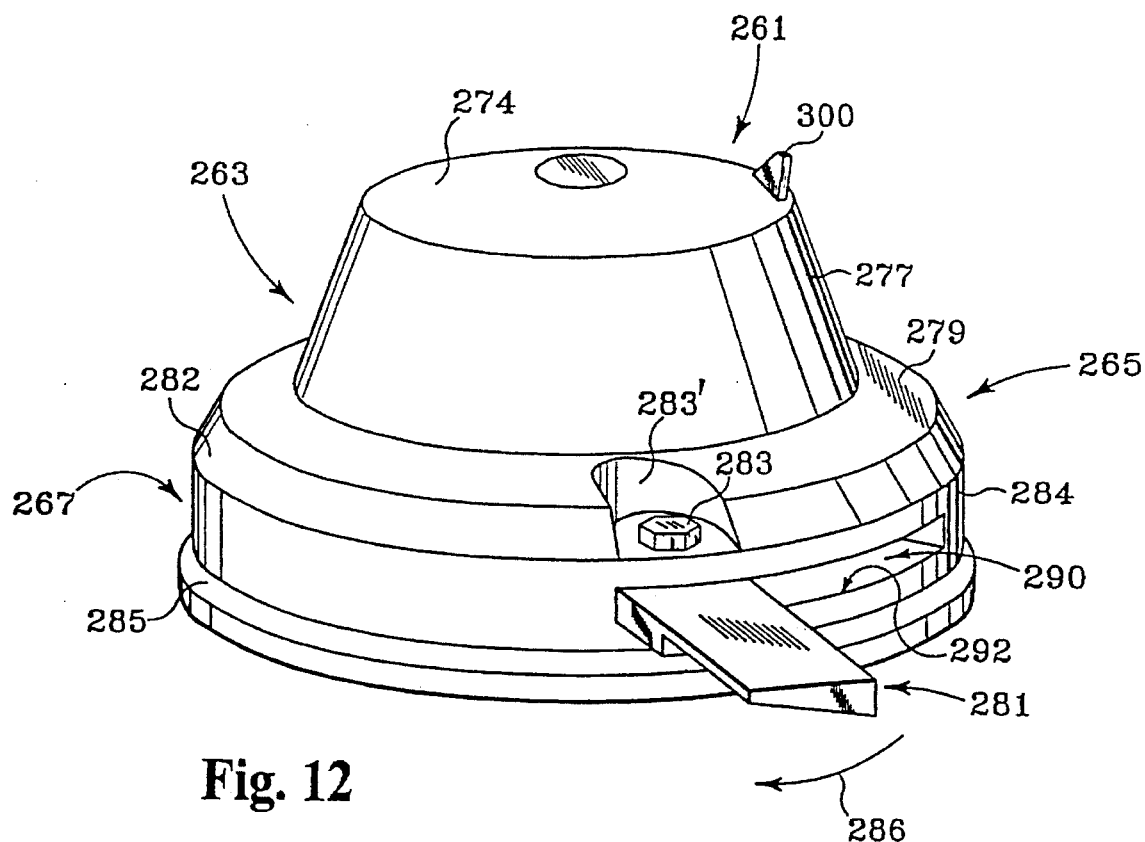
FIG. 12 is a perspective view of further embodiment of a rotating hub assembly of this invention.
Figure 13:
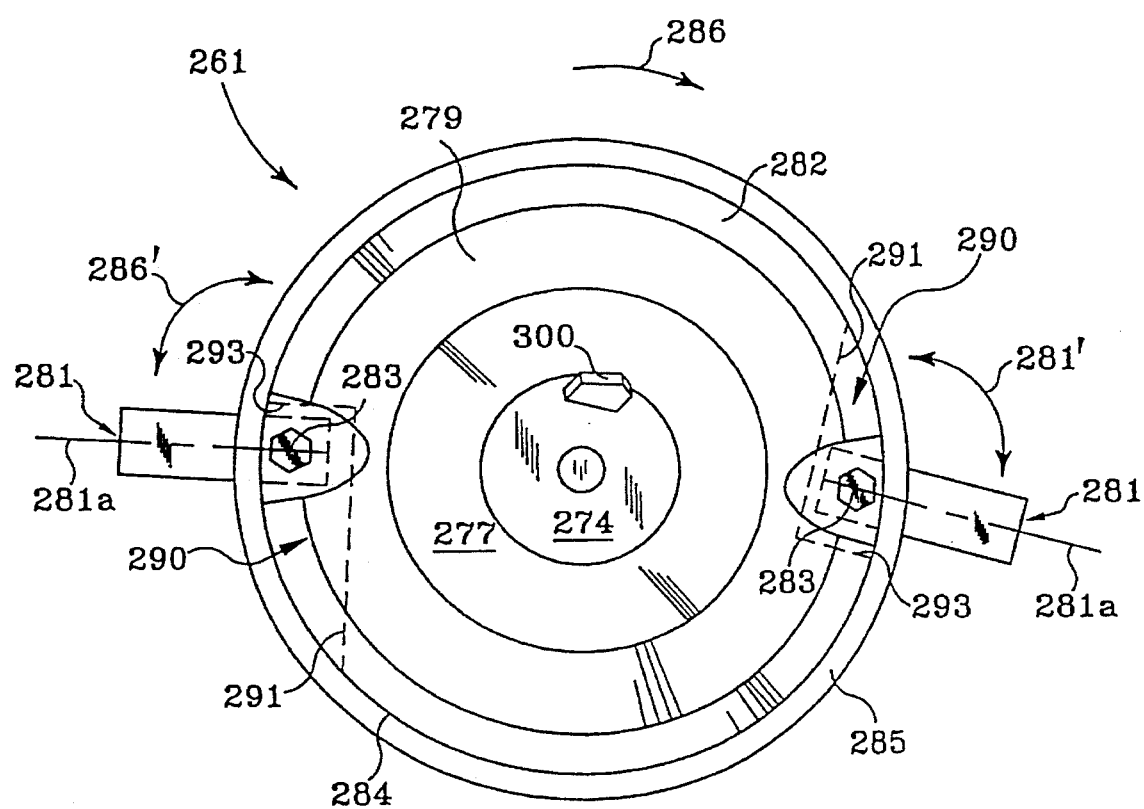
FIG. 13 is a top view of the rotating hub assembly of FIG. 12.

An preferred impeller hub assembly 261 suitable for use with this invention is shown in isolation in FIGS. 12 and 13. Impeller hub assembly 261 is located and supported within the flask housing in identical fashion as is impeller assemblies 61, 161 shown and described in relation to FIGS. 2 and 8, respectively. Impeller hub assembly 261 includes a rotating hub comprising a ring 285 disposed at the lower most portion 267 of the hub assembly 261 to prevent soft medical waste from being carried under hub assembly 261 while it rotates. In the preferred embodiment shown in FIGS. 12 and 13, the hub assembly 261 is formed with an upper portion 263, having preferably an inclined wall 277 and a lower portion 267 including a substantially cylindrical wall 284. An annular shoulder surface 279 disposed normally to the axis of rotation of hub 261 and an inclined frustoconical wall 282 extends between the upper portion 263 and lower portion 267.

A pair of blades 281 (only one blade is shown in FIG. 12) are pivotally mounted to the hub 261 at diametrically opposed locations on opposite sides of the hub 261 adjacent its lower portion 267 within recessed slots 290 provided in wall 284. Blade 281 is identical to blades 81, 181 as shown and discussed in relation to FIGS. 2 and 8, respectively. Blades 281 are pivotally secured by pins 283 formed by shoulder bolts extending through a receiving hole (not shown) provided near the inner end of the blade 281 and screwed into the lower surface 292 of slot 290. Bolts 283 are received in a recessed area 283 provided in the middle portion 265 of hub 261.

As shown in FIG. 13, slots 290 are formed in the sidewall 284 of hub 61 and extend inwardly toward the center of hub 261. Slots 290 include first forward impingement surfaces 293 and a second rear impingement surfaces 291. When the hub 261 is rotating in the direction shown by reference arrow 286 (clockwise), the pivotal blades 281 are urged to pivot outwardly along path 281 by centrifugal force to the extended position shown in FIG. 13. The blades 281 are prevented from pivoting forwardly in the direction of rotation (arrow 286) substantially past a reference line 281a extending radially outwardly from their pivotal mountings by the forward impingement surface 293 of recessed slot 290. Upon contact with stationary or more slowly moving waste material the blades 281 may pivot along reference path 281', partially received within slots 290, where the following edge of blade 281 impinges upon the second rear impingement surface 291 of slot 290.

Hub 261 shown in FIGS. 12 and 13 can further include a surface for breaking waste-carrying containers introduced into the waste treatment chamber. The container-breaking surface preferably comprises a spike or tooth-like member 300 equipped with a carbide metal tip and protruding upwardly and outwardly adjacent the outer edge of top surface 274 of the hub assembly 261. Spike 300 is effective in disintegrating waste-carrying containers made of thin polystyrene such as those described above.

Figure 14:
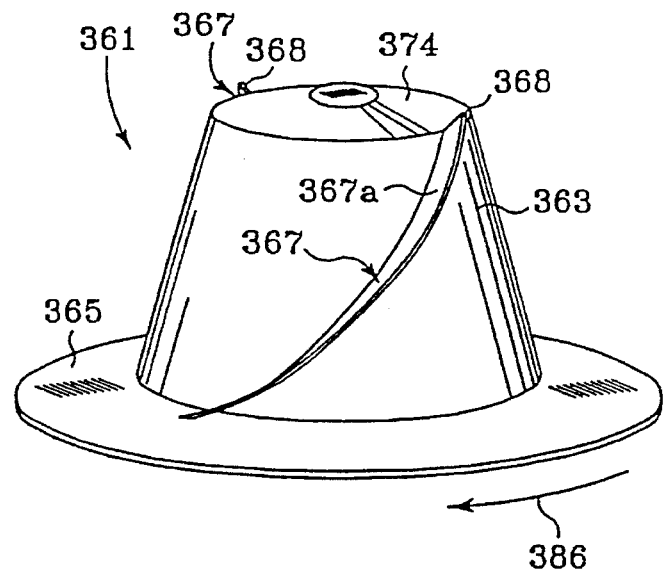
FIG. 14 is a perspective view of an alternative rotating hub provided in this invention.

This invention provides an alternative hub 361, shown in FIG. 14. The alternative hub 361 may replace the rotating hub assemblies described above when it is desirable to simply wash or disinfect the soft medical waste with a disinfectant prior to its disposal. Alternative hub 361 includes a generally frustoconical outer surface 363, a pair of fins 367 extending outwardly from the outer surface 363 of the hub 361 and a ring 365 extending outwardly from adjacent the lower edge of the outer surface 363. Ring 365 prevents the soft medical waste from being carried under the rotating hub 361, and also prevents waste materials from sitting idle on the bottom of the chamber during operation and thereby evading the washing and disinfection action of the apparatus. Fins 367 are disposed diametrically on opposite sides the outer surface 363 of hub 361 and partially form spiral-like surfaces 367a from adjacent the top surface 374 of hub 361 to the lower band 365. Each fin 367 has an upper tip 368 extending vertically above the top surface 374 of hub 363 which is adapted to tear open plastic refuse bags that are commonly used to tote soft medical waste, and to prevent materials from remaining adjacent on the top surface 374 of hub 362 while it is in operation. Thus, hub assembly 361 can effect the medical cleansing and disinfecting of soft medical waste.

The apparatus of the invention includes hub-mounting features permitting the rotating hubs to be replaced with little effort. As noted, hub assemblies 261 and 361 shown in FIGS. 12, 13 and 14, respectively, can be replaceably mounted and employed in the waste treatment apparatus of this invention described above and shown in FIGS. 2 and 8.

As with the apparatus shown in FIG. 2, the apparatus of FIGS. 8–14 includes a lower ball bearing assembly 166 and an upper ball bearing assembly 167 spaced several inches apart, and supported by, a bearing supporting cylinder 162, which is welded to the bottom of the flask assembly 151. The inner race of bearings 166 and 167 carry the impeller shaft 168. This assembly provides a rugged and durable rotatable support of the rotating waste destruction and treatment assembly (which includes pivotal blades 81, 181, 281 and rotating fenders and surfaces 211, 211b and 300), which must endure intense shock loads in operation. The combination of the pivotable blades, which are pivotally mounted intermediate the upper and lower bearings 166 and 167, and the spaced ball bearing support provided the impeller shaft provide a waste treatment assembly which can endure the torturous abuse imposed by the combined effects of solid and/or soft medical waste being processed.

Referring now to FIGS. 8 and 10, the motor 128 is securely mounted at its upper end to a support plate 126 which is carried by a plurality of vibration isolator couplings 124 to a pair of isolation bars 122 which are carried from the top 113 of the walled enclosure 310. A receiving plate 127 for the chamber-forming flask assembly 151 is carried above support plate 126 by a plurality of tubular spacers 129. The receiving plate 127 includes four spaced holes adapted to receive the four feet 158 of the flask assembly 151 in a manner like that described for the apparatus of FIG. 2. Receiving plate 127 has a central opening 130 which permits a driving coupling 138 from the rotating shaft 132 of the driving motor to extend into the keyed opening of the impeller shaft of the particular rotating hub assembly employed with the system. Thus, the entire rotational waste treatment assembly and its driving motor are suspended within the walled enclosure and openable top (FIG. 1) by a vibration isolating structure. There is no mechanical connection between the sidewalls 143 of the centralized tub portion 142 of the enclosure and the flask receiving plate 127 or any other portion of the waste treatment operating apparatus. An elastomeric gasket 144 is mounted to the opening in the centralized tub portion 142 of the apparatus enclosure. The elastomeric flange may be fastened to the sidewalls 143 of the centralized tub portion 142 by any convenient manner for example by an appropriate adhesive. The elastomeric gasket 144 and cylinder 213 tend to absorb and dampen vibration of the operating waste treatment assembly.

Thus, in the apparatus of the invention shown in FIGS. 8–14, vibration and sound are trapped and deadened in an improved manner within the enclosure for the apparatus, and the operating portion of the waste treatment apparatus including the flask assembly, driving motor and the intervening supporting structure, are isolated from the enclosure by elastomeric sound and vibration deadening elements. The driving motor and waste destruction chamber are thus isolated from the apparatus housing.

FIGS. 15–21 show another preferred medical waste collection station 410 of this invention.

Figure 15:
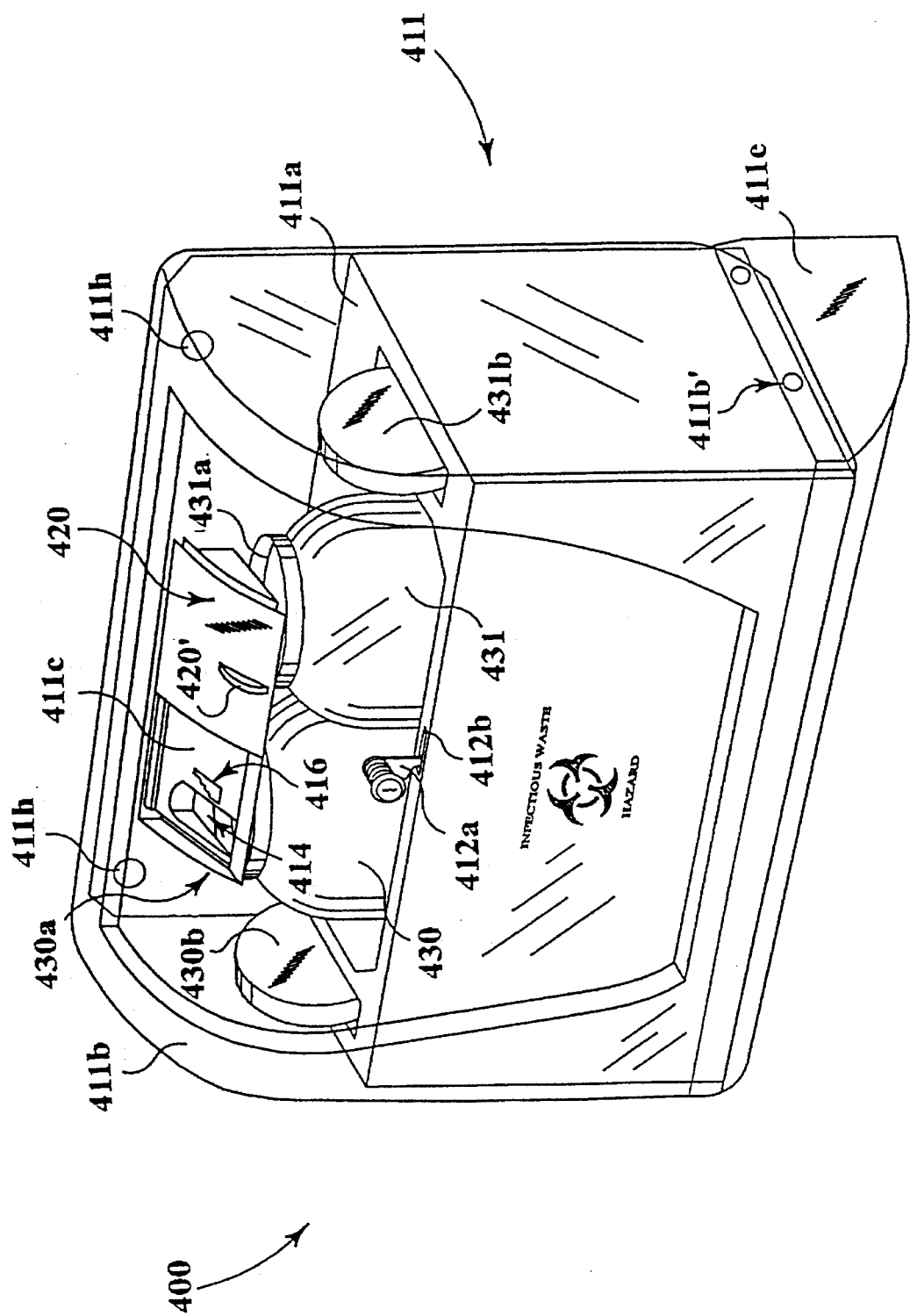
FIG. 15 is a perspective view of a medical waste collection station of the invention.
Figure 16:
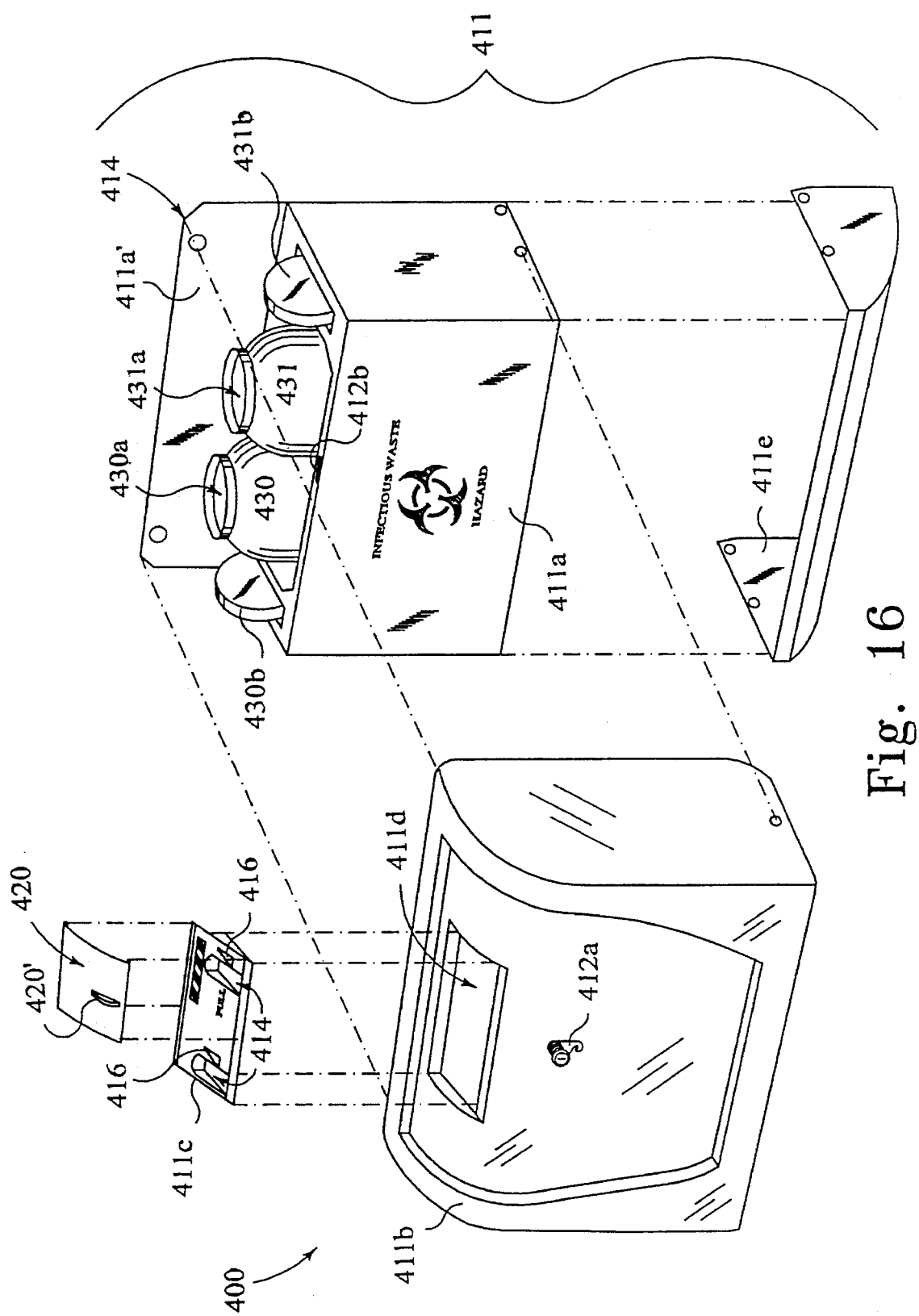
FIG. 16 is an exploded perspective view of the medical waste collection station of FIG. 15.
Figure 17:
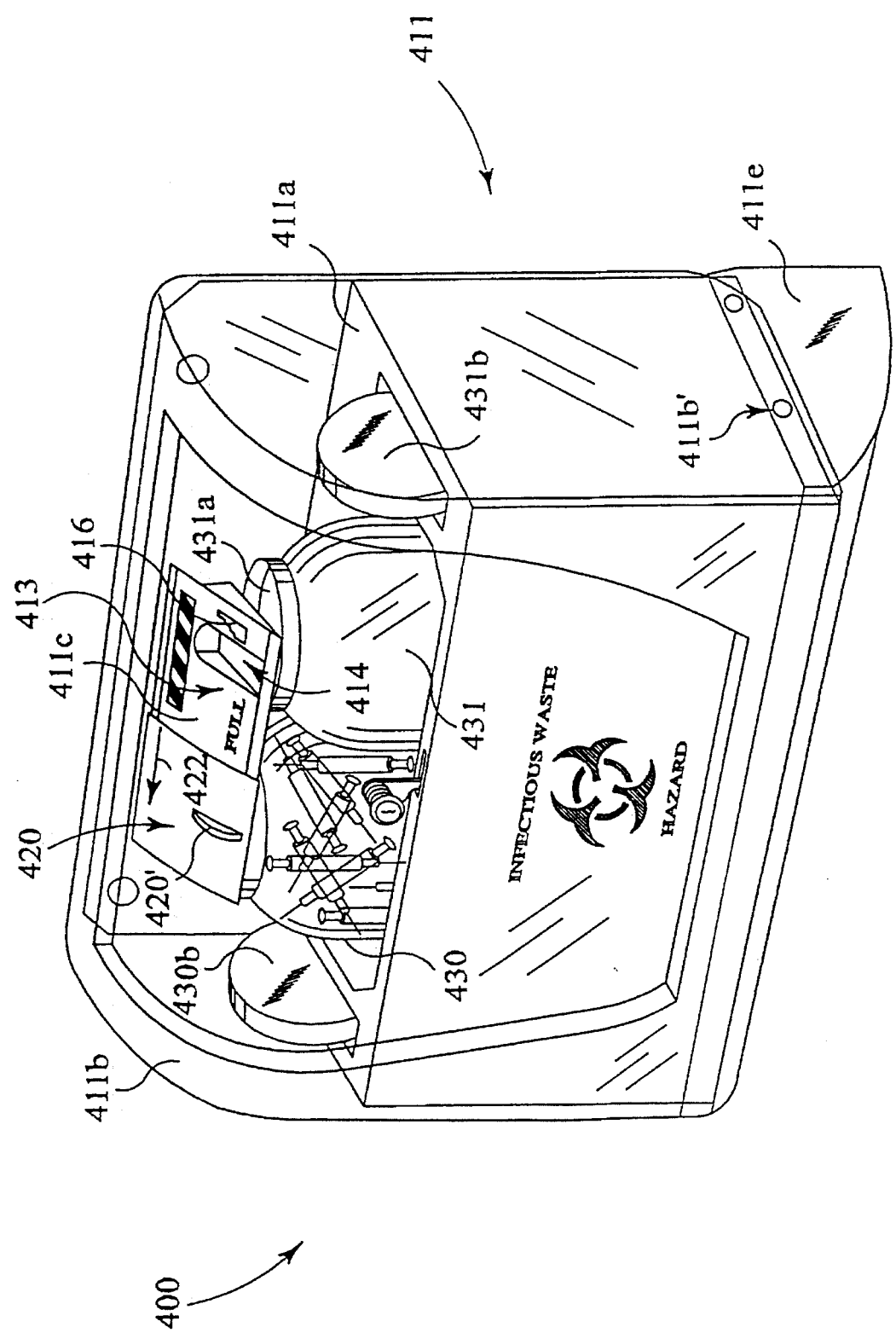
FIG. 17 is a perspective view of the medical waste collection station of this invention in use with one of the containers filled with medical waste.

As shown in FIGS. 15 and 16, the medical waste collection station of the invention includes first means 411 for supporting a plurality of medical waste containers 430, 431 and second means 420, carried by the first means 411, for sequentially providing access to the open tops 430a, 431a of all but one of the medical waste containers 430, 431 as shown in FIGS. 15 and 17.

The second means 420 preferably comprises movable means with the plurality of positions, each position of the movable means 420 allowing access to an open top 430a, 431a of only one of the medical waste containers 430, 431 while preventing access to the others.

In the preferred medical waste collection station in FIGS. 15–21 the first means 411 supports the plurality of medical waste containers 430, 431 with their open tops 430a, 431a lying generally in a horizontal plane, and carries the second means 420 over open tops 430a, 431a of the medical waste containers 430, 431. As shown in FIGS. 15 and 17, the second means 420 can preferably comprise a cover movably carried by the first means 411 over the horizontal plane generally including the open tops 430a, 431a and providing a plurality of positions, and the movable cover 420 provides access to the open top of a different medical waste container in each of the plurality of positions.

As indicated in FIG. 17, the first means 411 carries indicia 413 and the movable cover 420 is operatively associated with the indicia to provide notice when at least one of the medical waste containers 431 is full and ready to be replaced. As further indicated in FIG. 16 and 18a, the first means 411 includes a flat wall portion 414 which can be fastened to the building wall in an area where medical waste is generated.

In the preferred medical waste collection station 400 of FIGS. 15–18, the first means preferably forms a station enclosure 411 capable of supporting and enclosing at least two medical waste containers 430, 431 arranged side by side. More particularly, first means 411 preferably includes, as shown more clearly in FIG. 16, a base portion 411a for carrying containers 430,431 and their lids 430b and 431b, respectively, a shell portion 411b hingedly carried by base portion 411a, a cover plate 411c carried within a top opening 411d provided in shell portion 411b, and cover 420 slidably carried by plate 411c. If desired, a curved lower base portion or bottom facia 411e can be included. Shell portion 411b can be lockably secured by a key lock 412a carried thereon and adapted to be received in a lock-receiving slot 412b provided in base portion 411a and is hingedly carried at a pivot axis 411b and is movable, as shown by reference arrow 423, in FIGS. 18A and 18B, between an open position (FIG. 18A) and a closed position (FIG. 18B). In the open position as shown in FIG. 18A, medical personnel can access and remove the medical containers 430 and 431 carried therein, place the lid on the container (e.g., lid 431b on container 431), and transport the container filled with medical waste to the waste treatment apparatus of the invention. An empty container can then be placed in the collection station base portion 411a. The medical waste containers 430, 431 are supported by the station enclosure 411 with their open tops 430a, 431a below and adjacent to the top opening 411a provided in shell 411b. The second means, or movable cover, 420 is preferably slidably carried by the station enclosure 411 adjacent top opening 411d. The movable second means, or slidable cover, 420 is movable between a plurality of positions on plate 411c, with each position allowing access to a different single waste container 430, 431 through a plurality of separate depository openings 414 and otherwise blocking access to the other of the waste containers 430, 431. In FIG. 15, where the two medical waste containers 430, 431 are supported side by side, with their open tops 430a, 431a lying generally in a plane below the slidable cover 420, the slidable cover 420 is in a position over the open top 431a of container 431 and is slidable to a second position, where it exposes the open top of container 431 while covering the open top 430a of the other medical waste container 430.

Figure 20:
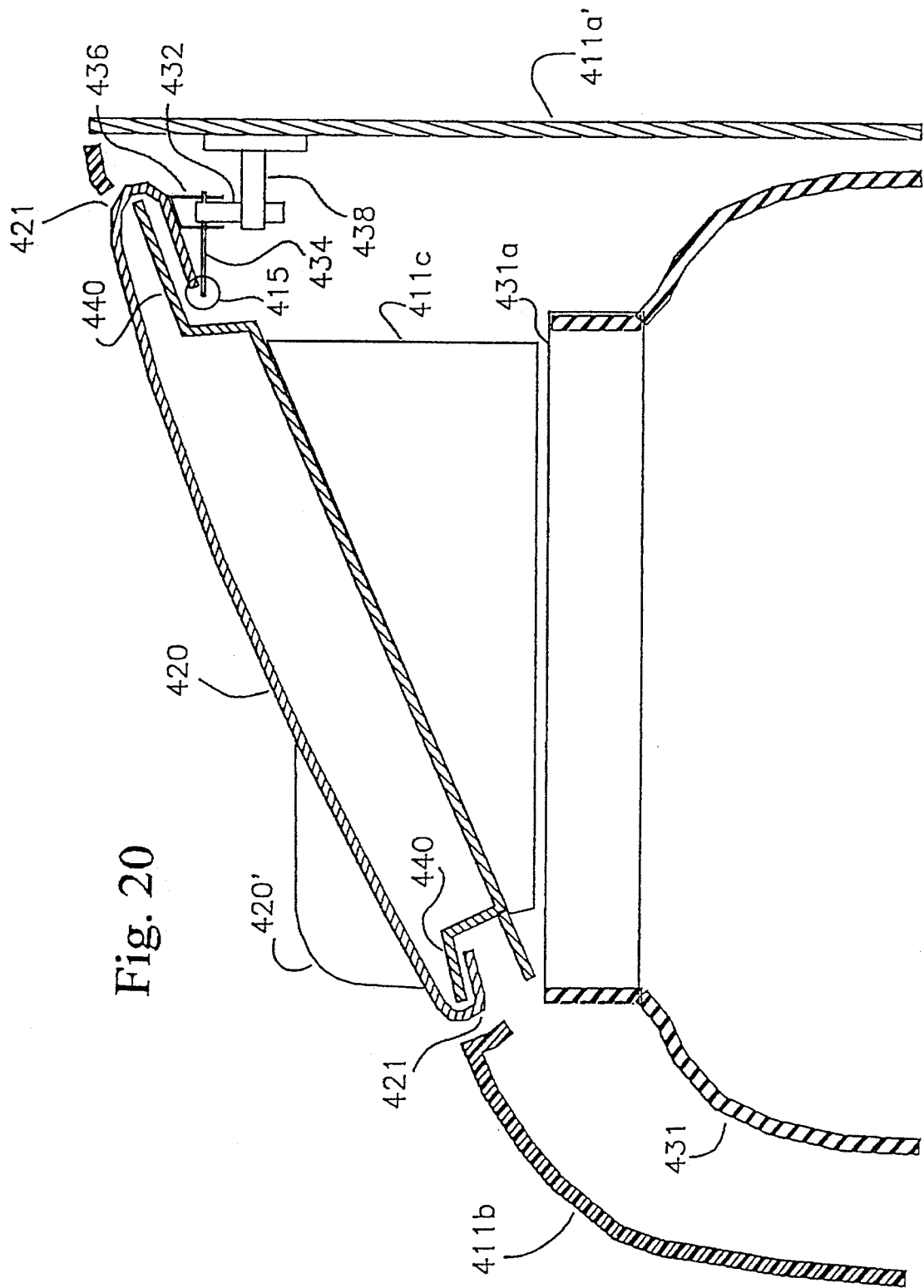
FIG. 20 is an enlarged partial side cross section of the upper portion of the medical waste collection station of the invention showing the means by which the slidable cover of the depository assembly can be secured.

Referring now to FIG. 20, in the medical waste collection station 400 of the invention the slidable cover 420 is engaged by a spring 415 which is coupled to and bears against a surface of the station enclosure 411 at one end and against a surface of the slidable cover 420 at the other end and is compressed between the engaged surfaces of the slidable cover 420 and the station enclosure 411 at all positions of the slidable cover. The slidable cover 420 can include a latch 432 extending downwardly from the slidable cover 420 and coupled thereto by a latch pivot post 434, which in turn is carried by a latch yoke 436 affixed to cover 420. Latch pivot post 434 is also coupled to one end of spring 415. The slidable cover 420 is urged by the spring 415 into a first position, at the right as shown in FIG. 15, where it extends over the open top 431a of one waste container 431 and exposes the open top 430a of the other waste container 430. When waste container 430 is filled, as depicted in FIG. 17, a user slides the slidable cover 420 to the left, as indicated by arrow 22 of FIG. 17, to its second position, where the latch 432 engages a stationary post 438 disposed on rear wall 411a, as shown in FIG. 20, to retain the slidable cover in the second position and to expose the open top 431a of waste container 431 through depository opening 414 of plate 411c. While the spring 415 is described as a compression spring, a tension spring can also be used with this invention with slight modification.

As shown in FIG. 17, the station enclosure 411 carries indicia 413 carried by cover plate 411c which is exposed when the second means, or slidable cover, 420 is in the second position (at the left of FIG. 17). Indicia 413 may be a brightly colored panel in red or yellow or in fluorescent (Da-Glo) colors, and the indicia 413 may be provided with lettering as shown in FIG. 17. The indicia 413 provides notice that when the second means, or slidable cover, 420 is in the second position, the first medical waste container 430 is full and ready to be replaced with an empty container.

Figure 19A:
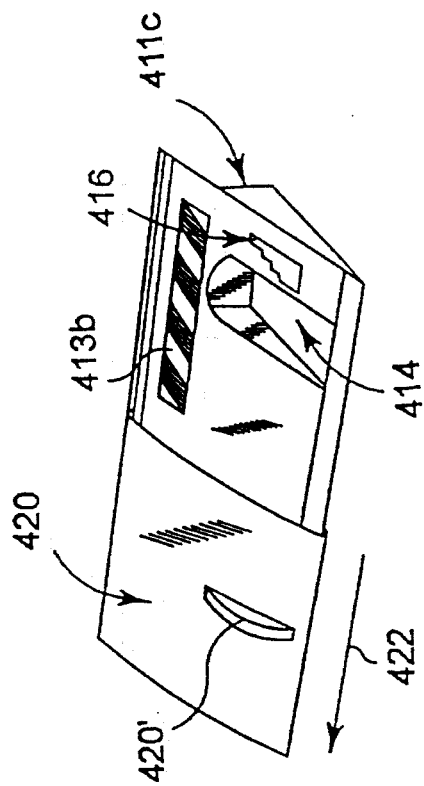
FIGS. 19A–19D illustrate various embodiments of the indicia means of the invention.
Figure 19B:
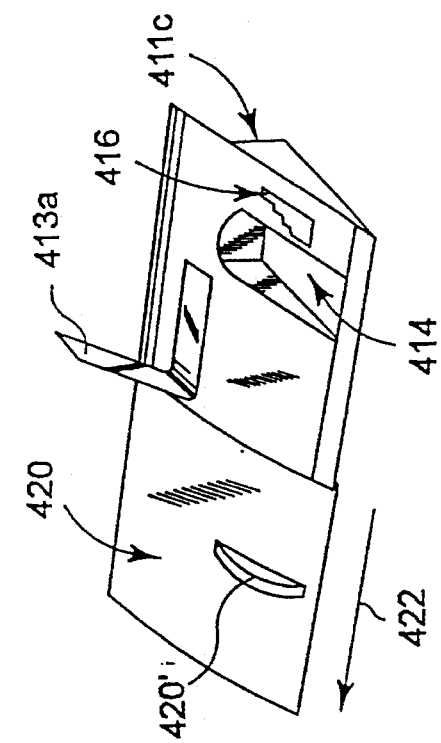
Figure 19C:
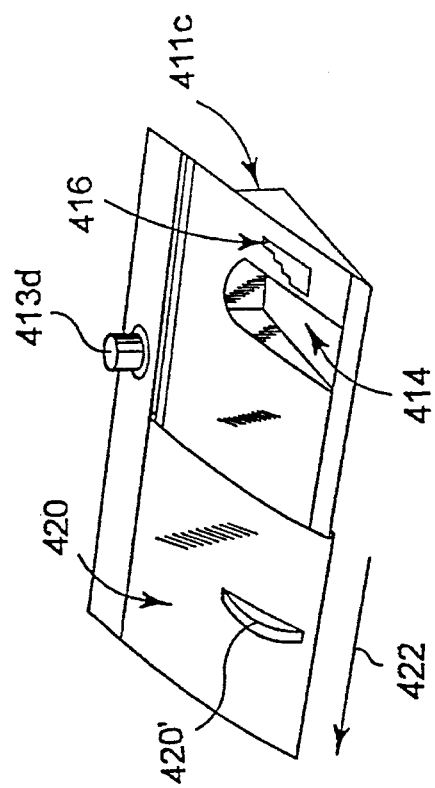
Figure 19D:
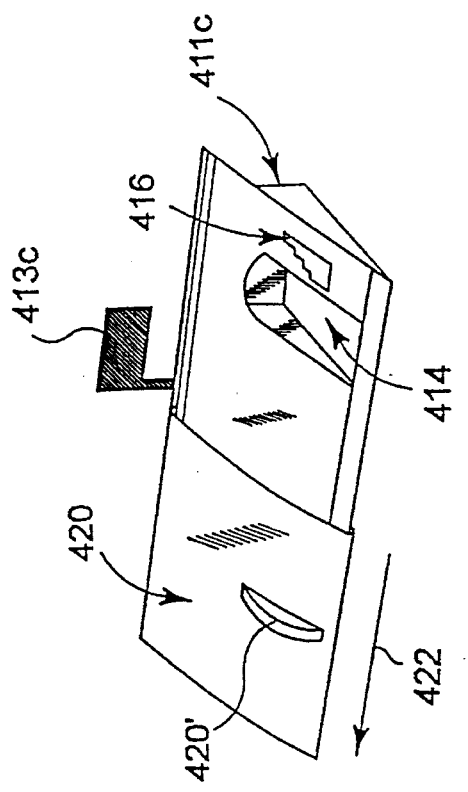

Indicia means 413 may take several forms as shown in FIGS. 19A–19D. In FIG. 19A, the indicia means may include a flip-up spring steel indicator 413a affixed to plate 411c that is urged to an "up" position as shown in FIG. 19A when cover 420 is moved in the direction of reference arrow 422. In FIG. 19B, the indicia means may include a brightly colored indicator strip or panel 413b as shown and discussed in relation to FIG. 17. In FIG. 19C, the indicia means may include a pop-up indicator flag 413c that is urged to an up position as shown in FIG. 19C when cover 420 is moved in the direction of reference arrow 422. In FIG. 19D, the indicia means can include a pop-up indicator button 413d that is urged to an up position as shown in FIG. 19D when cover 420 is moved in the direction of reference arrow 422.

As noted above, the back wall 411a of station enclosure 411 is preferably flat and provides means, such as slots or other screw fastener openings 411h, permitting the medical waste collection station 410 to be fastened to a building wall at a site of medical waste generation.

A further feature of medical waste collection stations of the invention is that the first means 411 can include surfaces adjacent the open ends of the medical waste containers to engage hypodermic needles and permit their disengagement from syringes and insertion into the medical waste containers without the need for human handling of the hypodermic needle. For example, as shown in the figures, the cover plate 411c of the first means 411 can form hypodermic needle engagement surfaces 416 over the open top, e.g. 431a, of a medical waste container, e.g. 431. The tooling surfaces 416 formed to engage a hypodermic needle can be slots of varying widths providing wrench surfaces to engage the standardly sized flats at the base of a hypodermic needle. The first means 411 and second means 420 are shaped to permit a user access to the tooling surfaces 416 of the station enclosure 411.

Thus, a user may dispose of a used hypodermic needle by inserting the hypodermic needle through the opening formed by tooling surfaces 416 and sliding the hypodermic needle into the tooling surfaces 416 until the needle engages the mating wrench surfaces so formed by the tooling surfaces and thereafter unscrewing or otherwise disengaging the hypodermic needle from the syringe and, with the syringe, pushing the used hypodermic needle from the slot and tool forming surfaces 416 into the waste container 431 below.

As shown in FIGS. 15–17, the base portion 411a of the collection station 411 is preferably formed from sheet metal, such as steel, and as shown in FIG. 17, blood and other fluids that may drain from needles and syringes into the bottom of the containers, and other unsightly medical waste are hidden from view so that installation of the collection station in areas accessible to non-medical personnel does not present a distasteful appearance.

The hinged shell portion 411b can be, preferably, formed from a strong, thermo-formed clear material, such as Lexan brand thermoplastic. Such a material provides effective structural support for the lock 412a, thus limiting access to containers 430, 431 and their contents to authorized medical personnel. In addition, the transparency of the shell portion 411b permits a user to see when one of the containers is full, as shown in FIG. 17, where the contents of container 430 are visible to a user because the container 430 is full and the user has moved the second means 420 to a position preventing over-filling of container 430 and opening container 431 to use.

In addition, the upper part of the shell portion and the cover plate 411c it carries, are forwardly angled at an acute angle, as shown in FIGS. 15–21 and most apparent from FIGS. 15 and 17. Because the cover plate 411c is carried at a forwardly facing acute angle, a user may readily see both the openings 414 providing access to the containers 430, 431 and the tooling surfaces 416 formed in the cover plate 411c that may be used to separate hypodermic needles from their syringes.

The collection station 400 of this invention can be, thus, relatively attractive, easy to use, and inexpensively made, can provide notice of, and prevent over-filling of, a filled container, can provide additional capacity for medical waste, can limit access to the medical containers and their contents through a locked cover and a restricted, but easily used, opening, and can provide automatic resetting of the means that prevents access to a filled container when the filled container is replaced.

It should be further noted that the invention does not require that the first means form an enclosure for the plurality of medical waste containers as shown and described with respect to FIGS. 15–21. The first means need only support the plurality of medical waste containers in operative association with the second means carried by the first means; however, in such instances where the first means forms an enclosure for the medical waste containers, the shell portion 411b of the station enclosure is preferably formed from transparent material permitting a user to visually examine the status, i.e., volume of medical waste material, of the medical waste containers, which are also preferably formed of transparent material.

It should be noted that the tooling surfaces 416 used to engage a hypodermic needle and disengage said hypodermic needle from a syringe need not be of the slotted configuration shown in FIGS. 15–17 but may be formed by a slot in any configuration that is suitable for engaging and holding the flatted surface at the base of a hypodermic needle. For example, wrench forming surfaces may be formed by a slot which narrows gradually to provide a range of substantially parallel opposing surfaces, variably spaced apart at a distance to accommodate the various standard hypodermic needles. In addition, separately formed tools for disengaging a used hypodermic needle may be attached to and carried by the first means 411.

Furthermore, a station enclosure may be provided with other types of removable or hinged walls to permit the insertion and withdrawal of the medical waste containers as needed.

The second means 420 of the invention can take many forms for providing selective and sequential access to the open tops of the plural medical waste containers one after the other(s). In addition to the slidable cover of the embodiment of FIGS. 15–21, the second means 420 can be a rotatable element, with an opening moved from position to position adjacent the open tops of circularly arranged containers, or the second means 420 can form a chute to direct medical waste to a selected one of the medical waste containers, e.g. for separate collection of different kinds of medical waste. In addition, the second means can comprise one or more movable internal valves to direct medical waste to a selected one of the plural waste containers, or a hinged door, to alternately cover the open tops of the plural waste containers.

Where the description above refers to used hypodermic needles, it should be recognized that not only the metal needle portion but the entire syringe assembly may be safely collected by this invention. In addition, disposable scalpels and other sharp solid medical waste and even soft medical waste may also be collected and safely disposed of. Following the collection of solid medical waste in a medical waste container, the entire container may be carried to and inserted in the waste treatment chamber for the treatment, as shown and described above.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected.

What is claimed is:

1. A medical waste collection station comprising:

a station enclosure for supporting and enclosing at least two waste containers arranged side by side, said station enclosure having a top opening formed therein;

at least two waste containers supported side by side within said station enclosure, each of said at least two waste containers having an open top and being supported by said station enclosure with their open tops below and adjacent the top opening of said station enclosure; and a movable element carried by said station enclosure adjacent the top opening for limiting access to only the open top of a single medical waste container through the top opening of said station enclosure, said movable element being movable between a plurality of positions, each position allowing access to a different single waste container and otherwise blocking access to the other waste containers.

2. The medical waste collection station of claim 1 further comprising indicia carried by said station enclosure and operatively associated with said movable element to indicate when a waste container is filled.

3. The medical waste collection station of claim 2 wherein said station enclosure has a planar backwall and means permitting the medical waste collection station to be carried by a building wall, and the station enclosure comprises a forward wall have an upper portion that is angled forwardly and downwardly to expose the top opening and indicia to view when the collection station is mounted on a building wall.

4. The medical waste collection station of claim 1 wherein said movable element comprises a movable cover slidably carried by said station enclosure and slidable between a plurality of positions, each position of the movable element providing access to only one of the containers.

5. The medical waste collection station of claim 4 wherein two medical waste containers are supported side by side with their open tops lying generally in a plane below the movable cover, and wherein said movable cover extends partially over the top opening of the station enclosure, is engaged by a spring and includes a latch portion extending downwardly therefrom, said movable cover being urged by said spring into a first position where it extends over a first one of the waste containers and exposes the open top of a second one of the waste containers, said movable cover being movable to a second position where its latch portion engages a stationary portion of the station enclosure to retain the movable cover in the second position where it extends over said second one of the waste containers, and exposes the open top of the first one of the waste containers.

6. The medical waste collection station of claim 5 wherein said station enclosure carries indicia, exposed by said movable cover when the movable cover is moved, to provide notice that a first container is full of medical waste.

7. The medical waste collection station of claim 1 wherein said station enclosure provides a hypodermic needle-engagement portion adjacent its top opening and over at least one of the at least two medical waste container open tops to permit a user to disengage a hypodermic needle from a syringe for insertion into a medical waste container without handling the needle.

8. A medical waste collection station, comprising:

first means for supporting a plurality of medical waste containers;

a plurality of separately removable medical waste containers supported by said first means, each said medical waste container having an open top; and second means, carried by said first means, that limits access to each of said medical waste containers to that medical waste container at any one time.

9. The medical waste collection station of claim 8 wherein said first means supports said plurality of medical waste containers with their open tops generally lying in a horizontal plane and is adapted to carry said second means over said horizontal plane.

10. The medical waste collection station of claim 8 wherein said first means includes an opaque base portion adapted to enclose the plurality of medical waste containers and carry lids for but separate from said medical waste containers.

11. A medical waste collection station, comprising:

first means for supporting a plurality of medical waste containers;

a plurality of medical waste containers supported by said first means, each said medical waste container having an open top; and second means, carried by said first means, for sequentially providing access to the open tops of the medical waste containers, wherein said second means comprises a movable cover carried adjacent the open tops of the medical waste containers and providing a plurality of positions, said cover providing access to the open top of a different individual medical waste container in each of the plurality of positions while preventing access to the open tops of the other medical waste containers.

12. A medical waste collection station, comprising:

first means for supporting a plurality of medical waste containers;

a plurality of medical waste containers supported by said first means, each said medical waste container having an open top; and second means, carried by said first means, for sequentially providing access to the open tops of the medical waste containers, wherein said first means supports said plurality of medical waste containers with their open tops generally lying in a horizontal plane and is adapted to carry said second means over said horizontal plane, and wherein said second means includes a cover movably carried over said horizontal plane to provide a plurality of positions, said cover providing access to the open top of a different medical waste container in each of the plurality of positions while preventing access to the open tops of the other medical waste containers.

13. A medical waste collection station, comprising:

first means for supporting a plurality of medical waste containers;

a plurality of medical waste containers supported by said first means, each said medical waste container having an open top; and second means, carried by said first means, for sequentially providing access to the open tops of the medical waste containers, wherein said first means includes indicia and said second means is operatively associated with said indicia to provide notice when at least one of the medical waste containers is full.

14. A medical waste collection station, comprising:

first means for supporting a plurality of medical waste containers, said first means including an opaque base portion adapted to enclose the plurality of medical waste containers and carry lids for, but separate from, said medical waste containers, and a transparent lockable shell portion hingedly carried by said opaque base portion;

a plurality of medical waste containers supported by said first means, each of said medical waste containers having an open top; and second means carried by said first means, for sequentially providing access to the open tops of the medical waste containers.

15. A medical waste collection station, comprising:

first means for supporting a plurality of medical waste containers;

a plurality of medical waste containers supported by said first means, each said medical waste container having an open top; and second means, carried by said first means, for sequentially providing access to the open tops of the medical waste containers, wherein said first means includes an opaque base portion adapted to enclose the plurality of medical waste containers and carry lids for, but separate from, said medical waste containers, wherein said first means further includes a transparent lockable shell portion hingedly carried by said opaque base portion, and wherein said lockable shell portion includes a cover plate including restricted openings providing access to said containers, and said second means comprises a cover slidably carried by said cover plate.

16. The medical waste collection station of claim 15 further comprising at least one needle-disengagement surface disposed in said cover plate over said horizontal plane and above the open top of at least one medical waste container, said slidable cover allowing access by a user to said needle-disengagement surface and the disengagement of used needles from syringes without the handling of the needle by the user.

17. The medical waste collection station of claim 16 wherein said upper portion of said transparent lockable shell portion carries said cover plate and said upper portion of said transparent lockable shell portion and cover plate are angled forwardly to provide a convenient line of sight to said restricted openings and needle disengagement surfaces.

18. A medical waste collection station, comprising;

first means for supporting a plurality of medical waste containers;

a plurality of medical waste containers supported by said first means, each said medical waste container having an open top; and second means, carried by said first means, for sequentially providing access to the open tops of the medical waste containers, wherein said first means includes an opaque base portion adapted to enclose the plurality of medical waste containers and carry lids for, but separate from, said medical waste containers, wherein said first means further includes a transparent lockable shell portion hingedly carried by said opaque base portion, and wherein said second means is a slidable cover carried by said hinged lockable shell portion; said slidable cover is engaged by a spring carried by said hinged lockable shell portion and includes a latch portion, said spring urging said slidable cover to a first position on said hinged lockable shell portion; and said opaque base portion includes a portion engaging the latch portion of said slidable cover when the slidable cover is moved to a second position to retain the slidable cover in the second position, through its engagement with the latch portion of a slidable cover, said latch portion of said slidable cover becoming disengaged from said engaging portion of the opaque base portion when the hinged lockable shell portion is opened by rotation on its hinges and said spring automatically resetting said slidable cover in its first position.

19. A medical waste collection station, comprising:

a plurality of medical waste containers having open tops;

means for supporting the plurality of medical waste containers with their open tops generally supported in a plane;

movable means carried by said supporting means adjacent the open tops of the medical waste containers, said movable means providing with said supporting means access to the open top of a different one of the plurality of medical waste containers as the movable means is moved through a plurality of positions with respect to said supporting means, and indicia carried by said supporting means and operatively associated with said movable means to indicate when one of the plurality of medical waste containers is filled.

20. The medical waste collection station of claim 19 wherein said movable means is slidably carried by said supporting means and includes means for retaining the movable means in a plurality of positions with respect to said support means.

21. A medical waste collection station, comprising:

a plurality of medical waste containers having open tops;

means for supporting the plurality of medical waste containers with their open tops generally supported in a plane; and movable means carried by said supporting means adjacent the open tops of the medical waste containers, said movable means providing with said supporting means access to the open top of a different one of the plurality of medical waste containers as the movable means is moved through a plurality of positions with respect to said supporting means, and tool surfaces disposed above and adjacent the top openings of said medical waste containers for engaging a hypodermic needle and permitting its disengagement from a syringe and its insertion into the medical waste containers without handling of the hypodermic needle by a user, said supporting means and said movable means cooperating to permit a user access to said tool surfaces.

22. A medical waste collection station, comprising:

one or more medical waste containers;

a station enclosure including an opaque first portion formed to support said one or more medical waste containers; and a transparent second portion forming, with said first portion, an enclosure for said one or more medical waste containers, said second portion including an opening permitting medical waste to be inserted into said one or more medical waste containers and surfaces formed to engage a hypodermic needle and permit its disengagement from a syringe for insertion into said one or more medical waste containers without the handling of the hypodermic needle by a user, said second portion including means for locking and unlocking the second portion to the first portion of said station enclosure.

* * * * *

UNITED STATES PATENT AND TRADEMARK OFFICE
CERTIFICATE OF CORRECTION

PATENT NO. : 5,465,841

DATED : November 14, 1995

INVENTOR(S) : Joseph H. Wilson, et al.

It is certified that error appears in the above-indentified patent and that said Letters Patent is hereby corrected as shown below:

In Col. 3, line 38, after "includes", insert --a container-breaking surface comprising a spike or--.

Signed and Sealed this

Twenty-fourth Day of September, 1996

Attest:

BRUCE LEHMAN

Attesting Officer     Commissioner of Patents and Trademarks